US011452295B2

(12) United States Patent
Fabbri et al.

(10) Patent No.: US 11,452,295 B2
(45) Date of Patent: Sep. 27, 2022

(54) COMPOSITION AND METHODS FOR REDUCING CORN-ON-CORN YIELD PENALTY

(71) Applicant: Monsanto Technology LLC, St. Louis, MO (US)

(72) Inventors: Bradon James Fabbri, Chesterfield, MO (US); Ken Ferreira, Wentzville, MO (US); Janne Kerovuo, St. Louis, MO (US); Matthew McCown, Wildwood, MO (US); Radha G. Mohanty, Ballwin, MO (US); Scott R. Schaecher, Webster Groves, MO (US)

(73) Assignee: Monsanto Technology LLC, St. Louis, MO (US)

( * ) Notice: Subject to any disclaimer, the term of this patent is extended or adjusted under 35 U.S.C. 154(b) by 1122 days.

(21) Appl. No.: 15/777,583

(22) PCT Filed: Nov. 17, 2016

(86) PCT No.: PCT/US2016/062531
§ 371 (c)(1),
(2) Date: May 18, 2018

(87) PCT Pub. No.: WO2017/087672
PCT Pub. Date: May 26, 2017

(65) Prior Publication Data
US 2019/0297898 A1 Oct. 3, 2019

Related U.S. Application Data

(60) Provisional application No. 62/258,118, filed on Nov. 20, 2015.

(51) Int. Cl.
*A01N 63/36* (2020.01)
*C12N 1/14* (2006.01)
*C12R 1/80* (2006.01)

(52) U.S. Cl.
CPC .............. *A01N 63/36* (2020.01); *C12N 1/14* (2013.01); *C12N 1/145* (2021.05); *C12R 2001/80* (2021.05)

(58) Field of Classification Search
CPC .......... A01N 63/36; C12N 1/145; C12N 1/14; C12R 2001/80
See application file for complete search history.

(56) References Cited

U.S. PATENT DOCUMENTS

| 4,536,207 A | 8/1985 | McCandliss et al. |
| 5,026,417 A | 6/1991 | Kucey |
| 5,484,464 A | 1/1996 | Gleddie et al. |
| 5,586,411 A | 12/1996 | Gleddie et al. |
| 5,965,545 A | 10/1999 | Ben-Shalom et al. |
| 7,241,588 B2 | 7/2007 | Chen et al. |
| 7,576,213 B2 | 8/2009 | Flematti et al. |
| 8,278,247 B2* | 10/2012 | Hnatowich ............ A01C 21/00 504/117 |
| 2009/0308121 A1* | 12/2009 | Reddy ..................... C05F 11/08 71/6 |
| 2010/0099560 A1 | 4/2010 | Hnatowich et al. |
| 2012/0322655 A1 | 12/2012 | Hnatowich et al. |
| 2014/0087944 A1* | 3/2014 | Habib .................... A01N 43/16 504/100 |
| 2014/0143909 A1 | 5/2014 | Greenshields et al. |
| 2014/0342905 A1 | 11/2014 | Bullis et al. |

FOREIGN PATENT DOCUMENTS

| RU | 2064231 C1 | 7/1996 |
| RU | 2286977 C2 | 11/2006 |
| WO | WO 2010/037228 | 4/2010 |
| WO | WO 2014/078647 | 5/2014 |

OTHER PUBLICATIONS

García-Fraile et al., PLoS ONE, May 2, 2012, vol. 7, Issue 5, e38122, p. 1-7.*
International Search Report of International Application No. PCT/US2016/062531 dated Jan. 31, 2017.
Janda et al., "16S rRNA Gene Sequencing for Bacterial Identification in the Diagnostic Laboratory: Pluses, Perils, and Pitfalls," *Journal of Clinical Microbiology*, 45(9):2761-2764 (2007).
Office Action dated May 8, 2020 issued in Australian Appln. 2016356777.
Office Action dated May 29, 2020 issued in Canadian Appln. 3,004,901.
Office Action dated May 29, 2020 issued in Chinese Appln. 201680078836.0 (with translation).
Wakeline et al., "The effect of Penicillium fungi on plant growth and phosphorus mobilization in neutral to alkaline soils from southern Australia," *Canadian Journal of Microbiology*, 53(1):106-115 (2007).
Extended European Search Report dated May 29, 2019, in European Application No. 16 86 7138.
Leggett et al., "Maize Yield Response to a Phosphorus-Solubilizing Microbial Inoculant in Field Trials," *J. Agricultural Sci.*, 153: 1464-1478 (2015).
Novozymes "A Unique Yield Enhancer from the World Leader in Bioinnovation," (2012) retrieved from the internet: url:https://www.legumematrix.com/images/56/3/JumpStart%20LCO%20(corn).pdf.
Cunningham et al., "Viability of *Penicillium bilaji* and *Colletotrichum gloeosporioides* conidia from liquid cultures," *Can. J. Bot.*, 68:2270-2274 (1990).
De Faria et al., "Mycoinsecticides and Mycoacaricides: A comprehensive list with worldwide coverage and international classification of formulation types," *Biol. Control*, 43:237-256 (2007).
Ding et al., "N credit of soybean to a following corn crop in central Ontario," *Can. J. Plant Sci.*, 78:29-33 (1998).

(Continued)

*Primary Examiner* — Kade Ariani
(74) *Attorney, Agent, or Firm* — Morrison & Foerster LLP

(57) ABSTRACT

Planting corn in one or more consecutive growing seasons in the same fields causes a yield reduction ("corn-on-corn yield penalty"). We developed methods and inoculants comprising *Penicillium bilaii*, to reduce corn-on-corn yield penalty. The disclosure covers the inoculants and methods for reducing corn-on-corn yield penalty.

29 Claims, 1 Drawing Sheet

(56) References Cited

OTHER PUBLICATIONS

Friesen et al., "Experimental determination of viability loss of *Penicillium bilaiae* condia during convective air-drying," *Appl. Microbiol. Biotechnol.*, 68:397-404 (2005).
Gentry et al., "Identifying Factors Controlling the Continuous Corn Yield Penalty," *Agron. J.*, 105(2):295-303 (2013).
Peterson et al., "Crop Yield as Affected by Rotation and Nitrogen Rate III. Corn," *Agron. J.*, 81:735-738 (1989).
Pochanavanich et al., "Fungal chitosan production and its characterization," *Lett. Appl. Microbiol.*, 35:17-21 (2002).
Shaw et al., "Perception of modification of plant flavonoid signals by rhizosphere microorganisms," *Environmental Microbiol.*, 8:1867-80 (2006).
Wilhelm et al., "Tillage and Rotation Interactions for Corn and Soybean Grain Yield as Affected by Precipitation and Air Temperature," *Agron. J.*, 96:425-432 (2004).
Diao et al., *Agricultural Microbial Engineering*, pp. 164-165 (2007).
Huang, "Chapter 14 Import and Export Business," *Dictionary of Economics and Trade* (1992).
Lu, "Northeast Farming System," *Textbooks for Agronomy and Agricultural Economics Majors* pp. 45-47 (date unknown).
Al-Kaisi et al., "Corn Following Corn Management," available online at https://crops(dot)extension(dot)iastate(dot)edu/encyclopedia/com-following-corn-management, downloaded (2021).
Baldock et al., "Manure and mineral fertilizer effects in continuous and rotational crop sequences in central New York," *Agron. J.* 72:511-518 (1980).
Shrader et al., "Estimation of a common nitrogen response for corn (*Zea mays*) in different crop rotations," *Argon. J.* 58:397-401 (1966).
Stanger et al., "Corn grain yield responses to crop rotation and nitrogen over 35 years," *Agron. J.* 100:643-650 (2008).

\* cited by examiner

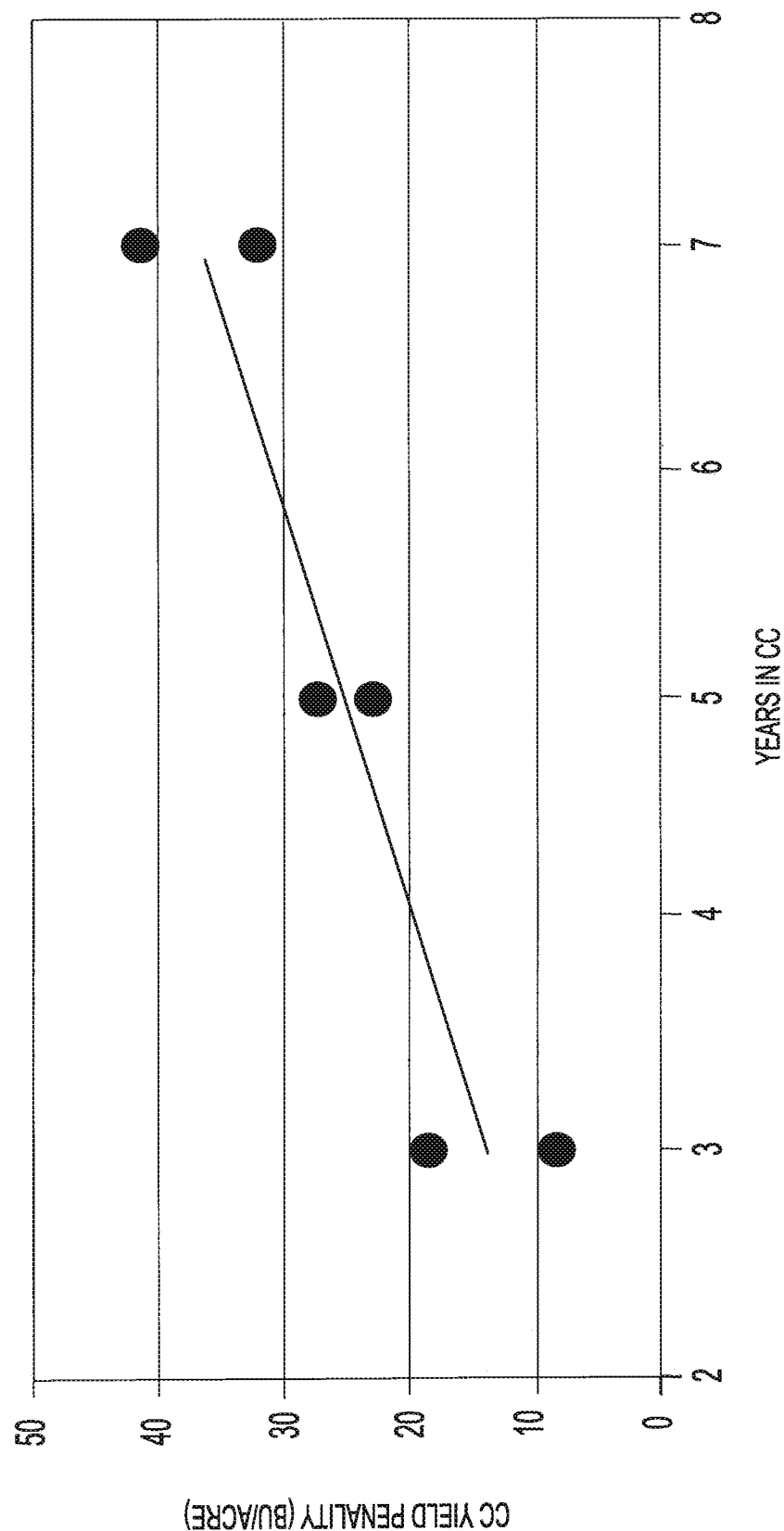

COMPOSITION AND METHODS FOR REDUCING CORN-ON-CORN YIELD PENALTY

This application is a U.S. National Stage Application of International Application No. PCT/US2016/062531, filed on Nov. 17, 2016, which claims the benefit of U.S. Provisional Application No. 62/258,118, filed on Nov. 20, 2015, each of which are incorporated by reference in their entireties herein.

FIELD

The present disclosure provides compositions and methods for reducing corn-on-corn yield penalty.

BACKGROUND

Corn-On-Corn Yield Penalty

Corn is widely cultivated throughout the world, and a greater weight of corn grain is produced each year than any other grain, with the U.S. producing 40% of the world's harvest. Typical yields for soybean, the second most commonly grown crop in the U.S., are only 28 to 34% of corn yields.

The utility of corn is multifaceted. Both grain and stover are used for animal feed and show promise as feedstocks for producing fermentation products. Through traditional or transgenic breeding efforts, corn varieties can be created to adapt to a range of environmental conditions and be resistant to a variety of pests and diseases.

Global demand for corn has grown steadily. Since 1924, corn yield has increased by seven fold with an annual yield growth rate of about 1.5% since 1970, due to improvements in hybrid, greater nitrogen (N) fertilizer rates, and other management practices.

In response to increasing international and domestic demand for U.S. corn grain, consecutive corn planting, namely, planting corn in two or more consecutive growing seasons in the same fields and not rotating with a different crop ("corn-on-corn"), has become a common practice in the U.S. Corn-on-corn production accounts for approximately 30% of the total baseline U.S. corn hectares in 2015 and as much as 50% of corn hectares in biofuel programs under the Energy Independence and Security Act (EISA) of 2007.

However, there are issues associated with corn-on-corn systems, such as reduced soil biological diversity, potentially causing a reduction in or loss of bio-control services and creating an even greater need for management techniques, including pesticides.

Moreover, it is widely accepted that yields decline in a corn-on-corn system as opposed to when corn is planted in rotation with soybean, wheat, or cotton. Id. This reduction is referred to as the corn-on-corn yield penalty. A 4-year study in eastern Nebraska under rainfed conditions showed that corn yields were 29% greater for corn grown in a 2-year soy-corn rotation than for corn in a continuous corn-on-corn monoculture. See, Peterson and Varvel, *Agron. J.*, 81: 735-738 (1989). In addition, a 16-year study has seen a 22% corn-on-corn yield penalty (compared to corn rotated with soybean) under rainfed conditions. See, Wilhelm and Wortmann, *Agron. J.*, 96: 425-432 (2004).

Reasons for corn-on-corn yield penalty are not fully understood, but weather, corn residue and nitrogen availability are often considered to play a role. See, Ding et al., *Can. J. Plant Sci.*, 78: 29-33 (1998).

Microorganisms

Plants extract a variety of elements, including nitrogen, phosphorous and micronutrients (e.g., copper, iron, zinc, etc.), from the media in which they grow.

Because many soils are deficient in such elements (and/or contain such elements in a form that is not readily available for plant uptake), nutritional supplements are commonly applied to soils in order to improve plant growth and yields. For example, phosphates are often added to soil to counteract a lack of available phosphorus. Although commercial fertilizers generally include a readily available source of phosphate, such as monoammonium phosphate or triple-super-phosphate, available forms of phosphate are rapidly converted in soil to relatively unavailable forms. It has been estimated that only 10 to 30% of phosphate fertilizer is used by the plant in the year it is applied, and one-third to one-half of the phosphate fertilizer applied may never be recovered by the plant.

Certain strains of *Penicillium* may be used to improve the availability of phosphorous in soil systems. See, e.g., U.S. Pat. Nos. 5,026,417; 5,484,464 and 7,241,588; and U.S. Patent Publication Nos. 2010/0099560 and 2014/0143909.

The present disclosure describes compositions and methods as effective ways to solve the problem of corn-on-corn yield penalty.

SUMMARY

The present disclosure includes compositions and methods for reducing corn-on-corn yield penalty. The present disclosure further provides that treatment with an inoculant comprising *Penicillium bilaii* results in reduction of corn-on-corn yield penalty. One advantage of an aspect of certain methods disclosed herein is that it provides an inoculant as an effective means of minimizing impact to yield without crop rotation, i.e. does not require a farmer to plant a second different crop in rotation.

The inoculants disclosed herein can be used in combination with other crop management systems.

The present disclosure also provides a method comprising: a) applying an inoculant comprising *Penicillium bilaii* to a population of corn plants or corn seeds in need of reducing a corn-on-corn yield penalty; and b) growing or planting the population of corn plants or corn seeds in need thereof in a field in which corn was grown during a growing season that immediately precedes planting of the population of corn plant or corn seeds in need thereof, where the inoculant is capable of reducing the corn-on-corn yield penalty.

Further provided by the present disclosure is a method comprising providing to a person a population of corn seeds in need of reducing a corn-on-corn yield penalty and an inoculant comprising an effective amount of *Penicillium bilaii*, where the amount is effective for reducing the corn-on-corn yield penalty.

In yet another aspect, the present disclosure includes a method for growing a population of corn plants, comprising selecting a field in which corn was grown during a growing season that immediately precedes selection of the field, planting corn seeds in need of reducing a corn-on-corn yield penalty treated with an inoculant comprising an effective amount of *Penicillium bilaii* in the selected field, where the amount is effective for reducing the corn-on-corn yield penalty.

The present disclosure also provides a method of preventing a corn-on-corn yield penalty in a population of corn plants in need thereof comprising: a) applying an inoculant comprising an effective amount of *Penicillium bilaii* to corn seeds and/or to a field in which corn was grown during a growing season that immediately precedes planting; and b) planting the corn seeds in the field without growing a population of non-corn plants in the field prior to planting the corn seeds, where the amount is effective to prevent the corn-on-corn yield penalty.

The present disclosure further provides a method of reducing a corn-on-corn yield penalty in a population of corn plants in need thereof comprising: a) applying an inoculant comprising an effective amount of *Penicillium bilaii* to corn seeds and/or to a field in which corn was grown during a growing season that immediately precedes planting of the corn seeds; and b) planting the corn seeds in the field without growing a population of non-corn plants in the field prior to planting the corn seeds, where the amount is effective to reduce the corn-on-corn yield penalty.

In a further aspect, the disclosure includes a method of enhancing corn yield in a field grown in a corn-on-corn rotation for two or more consecutive growing seasons, comprising: a) growing a first population of corn plants in the field during a first growing season; and b) growing a second population of corn plants in the field during a second growing season, where the second population of corn plants is treated with an inoculant comprising *Penicillium bilaii* prior to planting, at the time of planting and/or after planting, and where the first and second growing seasons are consecutive growing seasons.

In another aspect, the disclosure includes a method of reducing a corn-on-corn yield penalty in a field grown in a corn-on-corn rotation for two or more consecutive growing seasons, comprising: a) growing a first population of corn plants in the field during a first growing season; and b) growing a second population of corn plants in the field during a second growing season; the second population of corn plants is treated with an inoculant comprising *Penicillium bilaii* prior to planting, at the time of planting and/or after planting, and where the first and second growing seasons are consecutive growing seasons.

In a further aspect, the present disclosure includes a method of crop rotation management that provides for two consecutive corn plantings in a field where the later planting provides a yield that is at least 80%, 82%, 84%, 86%, 88%, 90%, 92%, 94%, 96%, 98%, 100%, 102%, 104%, 106%, 108%, 110%, 115%, 120%, or 125% of the yield of the earlier planting, the method comprising: a) treating corn seeds with an inoculant comprising an effective amount of *Penicillium bilaii*; and b) providing the treated corn seeds to a farmer for growing in a field in which corn was planted in an immediately preceding growing season.

The present disclosure further provides a method of reducing a corn-on-corn yield penalty, the method comprising: a) planting corn seeds in need thereof that have been treated with an inoculant comprising *Penicillium bilaii* in a field in which corn was grown during a growing season that immediately precedes planting of the corn seeds in need thereof; b) growing corn from the corn seeds in need thereof; and c) producing a yield of corn where the corn-on-corn yield penalty is reduced as a result of the inoculant comprising *Penicillium bilaii*.

In another aspect, the present disclosure includes a method of reducing the corn-on-corn yield penalty, the method comprising: a) administering, to a population of corn plants, corn seeds, and/or soil containing a population of corn plants or corn seeds in need thereof, an inoculant comprising an effective amount of *Penicillium bilaii*; and b) growing the population of corn plants or corn seeds in need thereof in the soil; where corn was grown in the soil during a growing season that immediately precedes growth of the population of corn plant or corn seeds.

In yet another aspect, the present disclosure further includes a method comprising: a) planting corn seeds in soil in which corn was grown during a growing season that immediately precedes planting of the corn seeds; and b) applying an inoculant comprising *Penicillium bilaii* to the soil, to the corn seeds and/or to plants that germinate from the corn seeds, where the inoculant is capable of increasing the yield of the plants.

Yet another aspect of the present disclosure includes a method of maximizing a field's farming revenue, the method comprising: a) determining a first projected net revenue from consecutive plantings of corn for at least two growing seasons in the field; b) determining a second projected net revenue from a corn on non-corn rotation in the field for the same number of growing seasons; c) determining a third projected net revenue from consecutive plantings of corn for at least two growing seasons in the field, where the third projected net revenue assumes that the corn and/or the field will be treated with an inoculant capable of reducing a corn-on-corn yield penalty in the field; d) comparing the first, second and third projected net revenues; e) recommending consecutive corn plantings; and f) providing corn seeds that have been treated with an inoculant comprising an effective amount of *Penicillium bilaii*.

In another aspect, the present disclosure includes a method comprising a) providing a farmer in need thereof with instructions for reducing a corn-on-corn yield penalty by applying an effective amount of an inoculant comprising *Penicillium bilaii* to a corn seed or to plants growing from the corn seed; and b) providing to the farmer the inoculant.

DESCRIPTION OF DRAWINGS

FIG. 1: Relationship between years in continuous corn and the continuous corn yield penalty. Adapted from Gentry et al., 2013.

DETAILED DESCRIPTION

Unless defined otherwise, technical and scientific terms as used herein have the same meaning as commonly understood by one of ordinary skill in the art. One skilled in the art will recognize many methods can be used in the practice of the present disclosure. Indeed, the present disclosure is in no way limited to the methods and materials described. Any references cited herein are incorporated by reference in their entireties. Singular forms "a," "an," and "the" are intended to include the plural forms as well, unless the context indicates otherwise.

As used herein, the term *Penicillium bilaii* is intended to include all iterations of the species name, such as "*Penicillium bilaiae*" and "*Penicillium bilaji*."

As used herein, "a population" means at least 100 plants, 200 plants, 500 plants, 1000 plants, 5000 plants, 10,000 plants, 50,000 plants, 100,000 plants, or more. In an aspect, a population of corn plants can be planted at least 1000 plants/acre, 5000 plants/acre, 10,000 plants/acre, 20,000 plants/acre, 50,000 plants/acre, 100,000 plants/acre, or more. In another aspect, a population of soybean plants can be planted at least 10,000 plants/acre, 20,000 plants/acre, 50,000 plants/acre, 100,000 plants/acre, 200,000 plants/acre, or more. In one aspect, a population of wheat plants can be planted at least 500,000 plants/acre. In further aspect, a population of cotton can be planted at least 50,000 plants/ acre. A person of ordinary skill in the art would understand the planting density for the plants referenced in the present disclosure.

As used herein, "a plant" means a population of plants grown in a field that produces a crop.

As used herein, "a population of corn seeds" may contain any number, weight or volume of corn seeds. For example, a population can contain at least, or greater than, about 10, 25, 50, 75, 100, 200, 300, 400, 500, 600, 700, 800, 900, 1000, 1500, 2000, 2500, 3000, 3500, 4000, 4500, 5000 or more corn seeds. Alternatively, the population can contain at least, or greater than, about 1 ounce, 5 ounces, 10, ounces, 1 pound, 2 pounds, 3 pounds, 4 pounds, 5 pounds, or more corn seeds. In one aspect, the population can contain at least 5 pounds, 10 pounds, 25 pounds, 50 pounds, 100 pounds, or more corn seeds. The present disclosure also provides a population of corn seeds with the inoculant comprising *Penicillium bilaii* in which at least 10%, 20%, 30%, 40%, 50%, 60%, 70%, 80%, 90%, or 100% of the seeds are provided with the inoculant.

Populations of corn seeds may be in any container available in the art. As used herein, "a container of corn seeds" may contain any number, weight or volume of corn seeds. For example, a container can contain at least, or greater than, about 10, 25, 50, 75, 100, 200, 300, 400, 500, 600, 700, 800, 900, 1000, 1500, 2000, 2500, 3000, 3500, 4000, 4500, 5000 or more corn seeds. Alternatively, the container can contain at least, or greater than, about 1 ounce, 5 ounces, 10, ounces, 1 pound, 2 pounds, 3 pounds, 4 pounds, 5 pounds, or more corn seeds. In one aspect, the container can contain at least 5 pounds, 10 pounds, 25 pounds, 50 pounds, 100 pounds, or more corn seeds. The present disclosure also provides a container of corn seeds with the inoculant comprising *Penicillium bilaii* in which at least 10%, 20%, 30%, 40%, 50%, 60%, 70%, 80%, 90%, or 100% of the seeds are provided with the inoculant. Containers of corn seeds may be any container available in the art.

As used herein, "an inoculant" includes any form of fungus and bacteria cells, amoeba, and archaea, mycelium or spores, which is capable of propagating on or in the soil when the conditions of temperature, moisture, etc., are favorable for microbial growth, thereby reducing a corn-on-corn yield penalty for a corn plant. In an aspect, the inoculant may include more than one microbe. In another aspect, the inoculant may not include microbes that are from various genera.

The present disclosure provides a method comprising: a) applying an inoculant comprising *Penicillium bilaii* to a population of corn plants or corn seeds in need of reducing a corn-on-corn yield penalty; and b) growing or planting the population of corn plants or corn seeds in need thereof in a field in which corn was grown during a growing season that immediately precedes planting of the population of corn plant or corn seeds in need thereof, where the inoculant is capable of reducing the corn-on-corn yield penalty.

In another aspect an inoculant comprises *Penicillium bilaii*. In one aspect a population of corn plants or part thereof is provided in an inoculant comprising *Penicillium bilaii*.

In another aspect, the *Penicillium bilaii* is present in an amount from $1 \times 10^1$ to $1 \times 10^{15}$ cfu/seed.

In an aspect, an effective amount of an inoculant comprising *Penicillium bilaii* is sufficient to cause a reduction of corn-on-corn yield penalty or other desired agricultural trait. The actual effective amount in absolute value depends on factors including, but not limited to, the size (e.g., the area, the total acreage, etc.) of the land for application with *Penicillium bilaii*, synergistic or antagonistic interactions between other active or inert ingredients.

Without being limited by any theory, *Penicillium bilaii* can in one aspect, activate symbiotic and developmental genes which results in a change in the root architecture or physiology of the plant. In another aspect, *Penicillium bilaii* drives the natural growth processes, which enhance crop performance.

In an aspect, the *Penicillium bilaii* is a known microorganism that has previously been deposited at the American Type Culture Collection in Rockville, Md., USA under the deposit number ATCC 22348 (1974 edition of the ATCC catalogue; under the name of "*Penicillium bilaiae*"). In the 1984 catalogue, the same deposit number is used for *Penicillium bilaii* and a further strain is identified by the deposit number 18309.

In another aspect, further isolates of *Penicillium bilaii* are deposited at the ATCC under the deposit number 20851 in accordance with the terms of the Budapest Treaty. In this deposit the fungus was named *P. bilaji* and the taxonomic details and its use has been described in U.S. Pat. No. 5,026,417. This strain has now been re-deposited as NRRL 50169. For complete information of the deposit see the last page of the description.

In further aspect, a new isolate of *Penicillium bilaii* was made as deposit number NRRL 50162. For complete information of the deposit see the last page of the description and the taxonomic details of this isolate and its proposed use is described in U.S. provisional application filed on Jan. 10, 2008 in the name of CSIRO.

In one aspect, other *Penicillium* spp. found to be useful according to the present disclosure are strains of *P. gaestrivorus*. One such strain is deposited as NRRL 50170.

In one aspect, the disclosure relates to a method of increasing the availability of phosphorus for plant uptake from soil, whose method comprises introducing into the soil an inoculant comprising *Penicillium bilaii*. The phosphorus may be provided from a source selected from the group consisting of sources originally present in the soil, and sources added to the soil as amendments and combinations thereof.

In another aspect, the inoculant further comprises a *Penicillium* fungus selected from the group consisting of *P. albidum, P. aurantiogriseum, P. chrysogenum, P. citreonigrum, P. citrinum, P. digitatum, P. frequentas, P. fuscum, P. gaestrivorus, P. glabrum, P. griseofulvum, P. implicatum, P. janthinellum, P. lilacinum, P. minioluteum, P. montanense, P. nigricans, P. oxalicum, P. pinetorum, P. pinophilum, P. purpurogenum, P. radicans, P. radicum, P. raistrickii, P. rugulosum, P. simplicissimum, P. solitum, P. variabile, P. velutinum, P. viridicatum, P. glaucum, P. fussiporus*, and *P. expansum*.

In another aspect, the *Penicillium bilaii* is selected from the group of deposited strains consisting of ATCC 20851, NRRL 50169, ATCC 22348, ATCC 18309, NRRL 50162. In further aspect, the *Penicillium bilaii* strains are NRRL 50169 and NRRL 50162. Non-limiting examples of *Penicillium bilaii* that may be useful in inoculants of the present disclosure include *Penicillium bilaii* ATCC 18309, *Penicillium bilaii* ATCC 20851, *Penicillium bilaii* ATCC 22348, *Penicillium bilaii* NRRL 50162, *Penicillium bilaii* NRRL 50169, *Penicillium bilaii* NRRL 50776, *Penicillium bilaii* NRRL 50777, *Penicillium bilaii* NRRL 50778, *Penicillium bilaii* NRRL 50779, *Penicillium bilaii* NRRL 50780, *Penicillium bilaii* NRRL 50781, *Penicillium bilaii* NRRL 50782, *Penicillium bilaii* NRRL 50783, *Penicillium bilaii* NRRL 50784, *Penicillium bilaii* NRRL 50785, *Penicillium bilaii* NRRL 50786, *Penicillium bilaii* NRRL 50787, *Penicillium bilaii* NRRL 50788, *Penicillium bilaii* RS7B-SD1 and combinations thereof, as well as *Penicillium bilaii* having at least at least 75%, 80%, 85%, 90%, 95%, 96%, 97%, 98%, 99% or more identity to any of the aforementioned strains on the basis of 16S rDNA sequence identity.

In one aspect, the *Penicillium* fungus according to the disclosure and in particular the specific strains, ATCC20851, NRRL 50169, NRRL 50170 and NRRL 50162 can be grown using solid state or liquid fermentation and a suitable carbon source. *Penicillium* isolates may be grown using any suitable method known to the person skilled in the art. For example, the fungus may be cultured on a solid growth medium such as potato dextrose agar or malt extract agar, or in flasks containing suitable liquid media such as Czapek-Dox medium or potato dextrose broth. These culture methods may be used in the preparation of an inoculant of *Penicillium* spp. for coating seeds and/or application to carrier to be applied to soil.

In an aspect, solid state production of *Penicillium* spores may be achieved by inoculating a solid medium such as a peat or vermiculite-based substrate, or grains including, but not limited to, oats, wheat, barley, or rice. The sterilized medium (achieved through autoclaving or irradiation) is inoculated with a spore suspension ($1 \times 10^2$-$1 \times 10^7$ cfu/ml) of the appropriate *Penicillium* spp. and the moisture adjusted to 20 to 50%, depending on the substrate. The material is incubated for 2 to 8 weeks at room temperature. The spores may also be produced by liquid fermentation (Cunningham et al., 1990. Can. J. Bot., 68:2270-2274). Liquid production may be achieved by cultivating the fungus in any suitable media, such as potato dextrose broth or sucrose yeast extract media, under appropriate pH and temperature conditions (as could be performed by anyone skilled in the art).

In another aspect, the resulting material may be used directly as a seed treatment, or the spores may be harvested, concentrated by centrifugation, formulated, and then dried using air drying, freeze drying, or fluid bed drying techniques (Friesen T., Hill G., Pugsley T., Holloway G., and Zimmerman D. 2005, Experimental determination of viability loss of *Penicillium bilaii* conidia during convective air-drying *Appl. Microbiol. Biotechnol.*, 68: 397-404) to produce a wettable powder. The wettable powder is then suspended in water, applied to the surface of seeds, and allowed to dry prior to planting. The wettable powder may be used in conjunction with other seed treatments, such as, but not limited to, chemical seed treatments, carriers (e.g., talc, clay, kaolin, silica gel, kaolinite) or polymers (e.g., methylcellulose, polyvinylpyrrolidone). Alternatively, a spore suspension of the appropriate *Penicillium* spp. may be applied to a suitable soil-cornpatible carrier (e.g., peat-based powder or granule) to appropriate final moisture content. The material is incubated at room temperature for 2 to 8 weeks and can then be applied to the soil in the furrow along with the seed.

In one aspect, a source of phosphorus is added to the soil. According to further aspects of the disclosure, the source of phosphorous comprises a source of phosphorous native to the soil or in another aspect the source of phosphorous is added to the soil. In one aspect, the source is rock phosphate. In another aspect, the source is a manufactured fertilizer.

Commercially available manufactured phosphate fertilizers are of many types. Some common ones are those containing monoammonium phosphate (MAP), triple super phosphate (TSP), diammonium phosphate, ordinary superphosphate, and ammonium polyphosphate. By means of the present disclosure it may be possible to reduce the amount of these fertilizers applied to the soil while still maintaining the same amount of phosphorus uptake from the soil.

In a further aspect, the source or phosphorus is organic. An organic fertilizer refers to a soil amendment derived from natural sources that guarantees, at least, the minimum percentages of nitrogen, phosphate, and potash. Examples include plant and animal by-products, rock powders, seaweed, inoculants, and conditioners. These are often available at garden centers and through horticultural supply companies. In particular, the organic source of phosphorus is from bone meal, meat meal, animal manure, compost, sewage sludge, guano, or mixtures thereof. Other fertilizers, such as nitrogen sources, or other soil amendments may of course also be added to the soil at approximately the same time as the *Penicillium* fungus or at other times, so long as the other materials are not toxic to the fungus.

Since the fungus has the effect of solubilizing phosphates which may already be present in soil (i.e., those which are native to the soil) and also those which are added to the soil, the fungus may be applied alone to soils which contain native sources of phosphorus, or may be applied to any soils in conjunction with added sources of phosphorus. The inoculants comprising the fungal strains according to the disclosure can, as described above, be provided using solid state or liquid fermentation and a suitable carbon source.

In an aspect, the amount of the inoculant to be applied to the soil is not limited in any particular respect. Clearly, if an insufficient amount is used, a noticeable effect will not be obtained. On the other hand, the use of large amounts of the inoculant will be wasteful because the amounts of phosphorus and/or micronutrients made available in the soil reach a maximum at a certain application rate and further additions beyond this rate do not give additional benefits. The suitable application rates vary according to the type of soil, the type of crop plants, the amounts of the source of phosphorus or micronutrients or both present in the soil or added thereto, etc. and a suitable rate can be found without difficulty by simple trial and error experiments for each particular case. Normally, the application rate falls into the range of 0.001-1.0 Kg fungal spores and mycelium (fresh weight) per hectare, $10^1$-$10^8$, or $10^2$-$10^6$ colony forming units (cfu) per seed (when coated seeds are used), or on a granular carrier applying between $1 \times 10^6$ and $1 \times 10^{11}$ colony forming units per hectare.

The fungal cells in the form of spores and optionally with a carrier can be added to a seed row of the soil at the root level or can be used to coat seeds prior to planting. When spores are added to the soil a granular formulation will be preferable. Formulations as liquid, peat, or wettable powder will be suitable for coating of seeds. When used to coat seeds, the material can be mixed with water, applied to the seeds and allowed to dry. Other carriers for the spores can be used to coat seeds. For example, the spores can be grown on moistened bran, dried, sieved and applied to seeds prior coated with an adhesive, e.g. gum arabic. The carrier should preferably be a soil compatible carrier. The term "soil-cornpatible" means any material which can be added to the soil without having an adverse effect on plant growth, soil structure, soil drainage or the like. Suitable carriers comprise, but are not limited to, wheat chaff, bran, ground wheat straw, peat-based powders or granules, gypsum-based granules, and clays (e.g., kaolin, bentonite, montmorillonite).

Suitable carriers include water, aqueous solutions, slurries, solids (e.g. peat, wheat, bran, vermiculite, and pasteurized soil) or dry powders. Particularly the carrier may in one aspect comprise a liquid containing a nutrient for the fungus.

The inoculant may contain additional additives including buffering agents, wetting agents, coating agents, and abrading agents.

In one aspect, a population of corn plants or corn seeds is provided in an inoculant. In one aspect, the inoculant is provided as a seed coating. In another aspect, the inoculant is provided to a planted seed, for example, in soil. In another aspect, the inoculant is provided to a green, above ground tissue, of a plant. In another aspect, one or more inoculants are applied to both the seed and a green tissue. In another aspect, different inoculants are applied to green tissue and seeds of the same plant. Such applications can be at similar times or growth stages or at different growth stages or times. Such applications can be timed to match environmental conditions.

In another aspect, the inoculant is applied to the corn seeds prior to planting. In another aspect, the inoculant is applied to the soil prior to planting. In another aspect, the inoculant is applied to the corn seeds at planting. In an aspect, the inoculant is provided to the corn seeds prior to the planting. In an aspect, the inoculant is applied to the soil prior to development stage V1. In an aspect, the inoculant is applied to the foliage of corn plants germinating from the corn seeds prior to development stage V1.

In an aspect, the applying of the inoculant is selected from the group consisting of coating the corn seeds with the inoculant prior to planting, applying the inoculant to the soil of the field prior to planting, applying the inoculant to the soil of the field at planting, applying the inoculant to the soil after planting, and applying the inoculant to the foliage of a population of corn plants growing in the field. In an aspect, the applying is applying the inoculant in-furrow. In an aspect, the applying is applying the inoculant to the population of corn seeds as a seed coating.

In one aspect the applying of any inoculant or method step can be performed in its entirety by a farmer, a farm worker, a laborer, a seed distributor, an agrochemical company, an agricultural technology company, or any other parties similarly situated.

In an aspect any seed or plant can be treated or used. In one aspect the seed is a corn seed and the plant is a corn plant. In one aspect, corn includes *Zea mays* or maize and includes all plant varieties that can be bred with corn. In another aspect a corn plant is a commercial plant available to farmers. In another aspect, a corn plant or seed can be an elite seed or plant. In another aspect, a corn plant can be a hybrid. In a further aspect a corn plant can be an inbred.

In one aspect, any appropriate plant part can be treated or used including plant organs (e.g., leaves, stems, roots, etc.), seeds, and plant cells and progeny of the same.

In another aspect, an inoculant can be in the form of a seed coating. Any appropriate seed coating can be used. In one aspect, liquid, slurry, or powder (e.g., wettable powder) form can be suitable for coating seeds. In one aspect, when used to coat seeds, the inoculant can be applied to the seeds and allowed to dry. In an aspect where the inoculant is a powder (e.g., a wettable powder), a liquid, such as water, can be added to the powder before application to a seed.

In another aspect, a treatment entails coating seeds with the at least two, three, four, five, or more inoculants. One illustrative process involves coating the inside wall of a round container with the inoculant, adding seeds, then rotating the container to cause the seeds to contact the wall and the inoculant, a process known in the art as "container coating." Seeds can be coated by combinations of coating methods. Soaking typically entails the use of an aqueous solution containing the plant growth enhancing agent. For example, seeds can be soaked for about 1 minute to about 24 hours (e.g., for at least 1 min, 5 min, 10 min, 20 min, 40 min, 80 min, 3 hr, 6 hr, 12 hr, or 24 hr). In one aspect, soaking is typically carried out for about 1 minute to about 20 minutes.

In one aspect seeds can be stored after application. In one aspect, the effectiveness of the seed coating can be retained for at least 50, 60, 70, 80, 90%, or more 6 months after the coating of the seeds with the inoculant.

In one aspect an inoculant, including those comprising *Penicillium bilaii* is capable of diffusing toward a young developing radical.

In one aspect, inoculants containing the *Penicillium bilaii* can further contain a sticking or coating agent. In one aspect, inoculants can further contain a coating polymer and/or a colorant.

In one aspect, at least two different inoculants are applied to seeds (directly or indirectly) or to the plant via the same inoculant (that is, they are formulated together). In one aspect, at least two different inoculants can be used. In an aspect, two different inoculants contain at least two different *Penicillium bilaii*. In at least one aspect, different inoculants can be formulated separately, and both inoculants are applied to a seed or plant. In another aspect, a different inoculant is applied to seeds than is applied to different parts of the plants, for example, without limitation, green tissue.

In one aspect, seeds can be treated with any inoculant and in a particular aspect a *Penicillium bilaii* in multiple ways including, without limitation, spraying or dripping. Spray and drip treatment can be conducted, for example, by formulating an effective amount of any inoculant including, without limitation, a *Penicillium bilaii* in an agronomically acceptable carrier, typically aqueous in nature, and spraying or dripping the inoculant onto seed via a continuous treating system (which is calibrated to apply treatment at a predefined rate in proportion to the continuous flow of seed), such as a drum-type of treater. Such methods include those that can advantageously employ relatively small volumes of carrier so as to allow for relatively fast drying of the treated seed. Large volumes of seeds can be efficiently treated. Batch systems, in which a predetermined batch size of seed and signal molecule inoculants are delivered into a mixer, can also be employed. Systems and apparatuses for performing these processes are commercially available from numerous suppliers, e.g., Bayer CropScience (Gustafson).

An inoculant can, in one aspect, comprise at least two, three, four, five, or more *Penicillium bilaii*, which can be applied just prior to, at the time of planting, or after planting. Treatment at the time of planting includes, without limitation, direct application to the seed and introducing the *Penicillium bilaii* into the soil. Such treatments include, without limitation, furrow treatment. In an aspect, seeds can be then packaged, e.g., in 50-lb or 100-lb bags, or bulk bags or containers, in accordance with standard techniques. In an aspect, treated seeds can be stored for at least 1, 2, 3, 4, 5, 6, 7, 8, 9, 10, 11, or 12 months, and even longer, e.g., 13, 14, 15, 16, 17, 18, 19, 20, 21, 22, 23, 24, 25, 26, 27, 28, 29, 30, 31, 32, 33, 34, 35, 36 months, or even longer, under appropriate storage conditions which are known in the art.

In one aspect, an inoculant contains an effective amount of an ingredient. In one aspect, an effective amount of the composition containing *Penicillium bilaii* used to treat the seed, expressed in units of weight, can be any amount but in one aspect ranges from about 1 to about 400 g/hundred weight (cwt) seed, and in another aspect from about 2 to about 70 g/cwt, and in a further aspect, from about 2.5 to about 3.0 g/cwt seed. In one aspect, the microorganism(s) is/are present in an amount ranging from about $1 \times 10^1$ to about $1\times10^{20}$ colony-forming units (cfu) per gram. For example, inoculant compositions of the present disclosure may comprise about $1\times10^1$, $1\times10$, $1\times10^3$, $1\times10^4$, $1\times10^5$, $1\times10^6$, $1\times10^7$, $1\times10^8$, $1\times10^9$, $1\times10^{10}$, $1\times10^{11}$, $1\times10^{12}$, $1\times10^{13}$, $1\times10^{14}$, $1\times10^{15}$ or more cfu of agriculturally beneficial microorganisms per seed (e.g., about $1\times10^4$ to about $1\times10^9$ cfu/g of *Penicillium bilaii*). In some embodiments, an effective amount of the composition containing *Penicillium bilaii* is/are present in an amount ranging from about $1\times10^1$ to about $1\times10^{20}$ cfu per oz. For example, inoculant compositions of the present disclosure may comprise about $1\times10^1$, $1\times10^2$, $1\times10^3$, $1\times10^4$, $1\times10^5$, $1\times10^6$, $1\times10^7$, 10, $1\times10^8$, $1\times10^9$, $1\times10^{10}$, $1\times10^{11}$, $1\times10^{12}$, $1\times10^{13}$, $1\times10^{14}$, $1\times10^{15}$ or more cfu of agriculturally beneficial microorganisms per oz of the inoculant composition (e.g., about $1\times10^4$ to about $1\times10^9$ cfu/oz of *Penicillium bilaii*).

In one aspect, a seed treatment can be direct or indirect. For purposes of indirect treatment of seed, it can include, without limitation, an in-furrow treatment, an effective amount of which can be any effective amount of the active ingredient and, in one aspect, the composition containing *Penicillium bilaii* can range from 1 g/acre to about 70 g/acre, and in another aspect, from about 50 g/acre to about 60 g/acre. For purposes of direct application to the plants, an effective amount can be any effective amount, and in one aspect and an effective amount of the composition containing *Penicillium bilaii* can range from 1 g/acre to about 30 g/acre, and in a further aspect, from about 11 g/acre to about 20 g/acre. In another aspect, the *Penicillium bilaii* inoculant can range from about $1\times10^6$ to about $1\times10^8$ cfu per pound of seeds. In one aspect, the *Penicillium bilaii* inoculant is present in an amount of about $1.7\times10^7$ cfu per pound of seeds.

In an aspect, the inoculant is coated on the seed, where the inoculant is coated at a rate in a range of about 0.25 to 1 fl ounces/cwt and in another embodiment at a rate of about 0.5 fl ounces/cwt (0.9 mg/seed) of an effective amount of the composition containing *Penicillium bilaii*.

In an aspect, the inoculant is applied in-furrow or to the soil of the field prior to planting at a rate in a range of about 8 to 16 ounces per acre.

In an aspect, the inoculant is applied to the foliage of a corn plant growing in the field at a rate of about 1, 2, 3, 4, 5, 6, 7, 8, 9, 10, 11, 12, 13, 14, 15, 16, 17, 18, 19, 20 or more ounces per acre of the composition containing *Penicillium bilaii*.

In another embodiment, the inoculants and methods described herein include a pesticide. The pesticide may be, for example, an insecticide, a fungicide, an herbicide, or a nematicide.

Microorganisms

In another aspect, microorganisms can be included in the inoculants and methods disclosed herein. Examples of microbes include bacteria from the genera *Rhizobium* spp. (e.g., *R. cellulosilyticum, R. daejeonense, R. etli, R. galegae, R. gallicum, R. giardinii, R. hainanense, R. huautlense, R. indigoferae, R. leguminosarum, R. loessense, R. lupini, R. lusitanum, R. meliloti, R. mongolense, R. miluonense, R. sullae, R tropici, R. undicola*, and/or *R. yanglingense*), *Bradyrhizobium* spp. (e.g., *B. bete, B. canariense, B. elkanii, B. iriomotense, B. japonicum, B. jicamae, B. liaoningense, B. pachyrhizi*, and/or *B. yuanmingense*), *Azorhizobium* spp. (e.g., *A. caulinodans* and/or *A. doebereinerae*), *Sinorhizobium* spp. (e.g., *S. abri, S. adhaerens, S. americanum, S. aboris, S. fredii, S. indiaense, S. kostiense, S. kummerowiae, S. medicae, S. meliloti, S. mexicanus, S. morelense, S. saheli, S. terangae*, and/or *S. xinjiangense*), *Mesorhizobium* spp., (*M. albiziae, M. amorphae, M. chacoense, M. ciceri, M. huakuii, M. loti, M. mediterraneum, M. pluifarium, M. septentrionale, M. temperatum*, and/or *M. tianshanense*), and combinations thereof. In further aspect, the microorganism is applied at a rate of about $1\times10^2$, $5\times10^2$, $1\times10^3$, $5\times10^3$, $1\times10^4$, $5\times10^4$, $1\times10^5$, $5\times10^5$, $1\times10^6$, $5\times10^6$, $1\times10^7$, $5\times10^7$, or $1\times10^8$ colony forming units per seed.

The inoculant can include an additional microorganism that improves organic P mobilization (phytase), nitrogen use efficiency, micronutrient availability, or a phosphate solubilizing microorganism.

As used herein, the term "phosphate solubilizing" is intended to mean the conversion of insoluble phosphate (e.g., rock phosphate, etc.) into a soluble phosphate form.

As used herein, "phosphate solubilizing microorganism" is a microorganism that is able to increase the amount of phosphorous available for a plant, including but not limited to, increasing phosphorous in the soil. Phosphate solubilizing microorganisms include fungal and bacterial microbial species. Non-limiting examples of phosphate solubilizing microorganisms include, without limitation, species from a genus selected from the group consisting of *Acinetobacter, Arthrobacter, Arthrobotrys, Aspergillus, Azospirillum, Bacillus, Burkholderia, chryseomonas, Enterobacter, Eupenicillium, Exiguobacterium, Klebsiella, Kluyvera, Microbacterium, Mucor, Paecilomyces, Paenibacillus, Pseudomonas, Serratia, Stenotrophomonas, Streptomyces, Streptosporangium, Swaminathania, Thiobacillus, Torulospora, Vibrio, Xanthobacter*, and *Xanthomonas*.

Non-limiting examples of phosphate solubilizing microorganisms can be also selected from the group consisting of *Acinetobacter calcoaceticus, Acinetobacter* sp, *Arthrobacter* sp., *Arthrobotrys oligospora, Aspergillus niger, Aspergillus* sp., *Azospirillum halopraeferans, Bacillus amyloliquefaciens, Bacillus atrophaeus, Bacillus circulans, Bacillus licheniformis, Bacillus subtilis, Burkholderia cepacia, Burkholderia vietnamiensis, Candida krissii, Chryseomonas luteola, Enterobacter aerogenes, Enterobacter asburiae, Enterobacter* sp., *Enterobacter taylorae, Eupenicillium parvum, Exiguohacterium* sp., *Klebsiella* sp., *Kluyvera cryocrescens, Microbacterium* sp., *Mucor ramosissimus, Paecilomyces hepialid, Paecilomyces marquandii, Paenibacillus macerans, Paenibacillus mucilaginosus, Pantoea aglomerans, Penicillium expansum, Pseudomonas corrugate, Pseudomonas fluorescens, Pseudomonas lutea, Pseudomonas poae, Pseudomonas putida, Pseudomonas stutzeri, Pseudomonas trivialis, Serratia marcescens, Stenotrophomonas maltophilia, Streptomyces* sp., *Streptosporangium* sp., *Swaminathania salitolerans, Thiobacillus ferrooxidans, Torulospora globosa, Vibrio proteolyticus, Xanthobacter agilis*, and *Xanthomonas campestris*.

Herbicides

As used herein, the term "herbicide(s)" means any agent or combination of agents capable of killing weeds and/or inhibiting the growth of weeds (the inhibition being reversible under certain conditions). Herbicides can be utilized in an aspect of the present disclosure. In one aspect, a herbicide can be used in combination with either an inoculant of the present disclosure or a part of a method of the present disclosure.

Suitable herbicides used in the inoculants and methods disclosed herein include acetochlor, clethodim, dicamba, flumioxazin, fomesafen, mesotrione, quizalofop, saflufenacil, sulcotrione, S-3100 and 2,4-D, bentazon, acifluorfen, chlorimuron, lactofen, clomazone, fluazifop, glufosinate, glyphosate, sethoxydim, imazethapyr, imazamox, fomesafe, flumiclorac, imazaquin, and clethodim. Commercial products containing each of these compounds are readily available. Herbicide concentration in the inoculant will generally correspond to the labeled use rate for a particular herbicide.

In one aspect, the inoculants described herein can further comprise one or more herbicides. Suitable herbicides include, without limitation, chemical herbicides, natural herbicides (e.g., bioherbicides, organic herbicides, etc.), or combinations thereof. Non-limiting examples of suitable herbicides include, without limitation, bentazon, acifluorfen, chlorimuron, lactofen, clomazone, fluazifop, glufosinate, glyphosate, sethoxydim, imazethapyr, imazamox, fomesafe, flumiclorac, imazaquin, clethodim, pendimethalin; 3,4-Dimethyl-2,6-dinitro-N-pentan-3-yl-aniline; N-(1-ethylpropyl)-2,6-dinitro-3,4-xylidine; pronamide; propyzamide; 3,5-Dichloro-N-(1,1-dimethylpropynyl)benzamide; 3,5-Dichloro-N—(1,1-dimethyl-2-propynyl)benzamide; N-(1,1-Dimethylpropynyl)-3,5-dichlorobenzamide; S-ethyl N-ethylthiocyclohexanecarbamate; trifluralin; 2,6-Dinitro-N,N-dipropyl-4-(trifluoromethyl)aniline; glyphosate; N-(phosphonomethyl)glycine; and derivatives thereof. In one aspect, the one or more herbicides for use in accordance with this disclosure include, without limitation, pronamide (commercially referred to as Kerb®); propyzamide; 3,5-Dichloro-N-(1,1-dimethylpropynyl)benzamide; 3,5-Dichloro-N-(1,1-dimethyl-2-propynyl)benzamide; N-(1,1-Dimethylpropynyl)-3,5-dichlorobenzamide; cycloate, S-ethyl N-ethylthiocyclohexanecarbamate (commercially referred to as Ro-Neet®); trifluralin; 2,6-Dinitro-N,N-dipropyl-4-(trifluoromethyl)aniline; glyphosate; N-(phosphonomethyl) glycine; and derivatives thereof. Commercial products containing each of these compounds are readily available. Herbicide concentration in the inoculant will generally correspond to the labeled use rate for a particular herbicide.

Fungicide(s)

As used herein, the term "fungicide(s)" means any agent or combination of agents capable of killing fungi and/or inhibiting fungal growth. Fungicides can be utilized in an aspect of the present disclosure. In one aspect, fungicide can be used in combination with either an inoculant of the present disclosure or a part of a method of the present disclosure.

In one aspect, the inoculants described herein can further comprise one or more fungicides. Fungicides useful to the inoculants described herein will suitably exhibit activity against a broad range of pathogens, including but not limited to *Phytophthora, Rhizoctonia, Fusarium, Pythium, Phomopsis*, or *Selerotinia* and *Phakopsora*, and combinations thereof.

Non-limiting examples of useful fungicides include aromatic hydrocarbons, benzimidazoles, benzthiadiazole, carboxamides, carboxylic acid amides, morpholines, phenylamides, phosphonates, quinone outside inhibitors (e.g. strobilurins), thiazolidines, thiophanates, thiophene carboxamides, and triazoles. Particular examples of fungicides include acibenzolar-S-methyl, azoxystrobin, benalaxyl, bixafen, boscalid, carbendazim, cyproconazole, dimethomorph, epoxiconazole, fludioxonil, fluopyram, fluoxastrobin, flutianil, flutolanil, fluxapyroxad, fosetyl-Al, ipconazole, isopyrazam, kresoxim-methyl, mefenoxam, metalaxyl, metconazole, myclobutanil, orysastrobin, penflufen, penthiopyrad, picoxystrobin, propiconazole, prothioconazole, pyraclostrobin, sedaxane, silthiofam, tebuconazole, thiabendazole, thifluzamide, thiophanate, tolclofos-methyl, trifloxystrobin, and triticonazole. In one aspect, the fungicides include pyraclostrobin, propiconazole, trifloxystrobin, azoxystrobin, fluxapyroxad, and combinations thereof.

Non-limiting examples of commercial fungicides which can be suitable for the inoculants disclosed herein include, without limitation, PROTÉGÉ, RIVAL or ALLEGIANCE FL or LS (Gustafson, Plano, Tex.), WARDEN RTA (Agrilance, St. Paul, Minn.), APRON XL, APRON MAXX RTA or RFC, MAXIM 4FS or XL (Syngenta, Wilmington, Del.), CAPTAN (Arvesta, Guelph, Ontario) and PROTREAT (Nitragin Argentina, Buenos Ares, Argentina). Active ingredients in these and other commercial fungicides include, but are not limited to, fludioxonil, mefenoxam, azoxystrobin and metalaxyl. Commercial fungicides are most suitably used in accordance with the manufacturer's instructions at the recommended concentrations.

Insecticide(s)/Nemacide(s)/Acaricide(s)

As used herein, the term "insecticide(s)" means any agent or combination of agents capable of killing one or more insects and/or inhibiting the growth of one or more insects. Insecticides can be utilized in an aspect of the present disclosure. In one aspect, an insecticide, nematicide, or acaricide can be used in combination with either an inoculant of the present disclosure or a part of a method of the present disclosure.

As used herein, the term "nematicide(s)" means any agent or combination of agents capable of killing one or more nematodes and/or inhibiting the growth of one or more nematodes. Nematicides can be utilized in an aspect of the present disclosure.

As used herein, the term "acaricide(s)" means any agent or combination of agents capable of killing one or more acarids and/or inhibiting the growth of one or more acarids. Acaricides can be utilized in an aspect of the present disclosure.

In one aspect, the inoculants described herein can further comprise one or more insecticides, acaricides, nematicides, or combinations thereof. Insecticides useful to the inoculants described herein will suitably exhibit activity against a broad range of insects including, but not limited to, wireworms, cutworms, grubs, corn rootworm, seed corn maggots, flea beetles, chinch bugs, aphids, leaf beetles, stink bugs, and combinations thereof. The insecticides, acaricides, and nematicides described herein can be chemical or natural (e.g., biological solutions such as fungal pesticides, etc.).

Non-limiting examples of insecticides and nematicides include carbamates, diamides, macrocyclic lactones, neonicotinoids, organophosphates, phenylpyrazoles, pyrethrins, spinosyns, synthetic pyrethroids, tetronic and tetramic acids. In particular embodiments insecticides and nematicides include abamectin, aldicarb, aldoxycarb, bifenthrin, carbofuran, chlorantraniliporle, chlothianidin, cyfluthrin, cyhalothrin, cypermethrin, cyantraniliprole, deltamethrin, dinotefuran, emamectin, ethiprole, fenamiphos, fipronil, flubendiamide, fosthiazate, imidacloprid, ivermectin, lambda-cyhalothrin, milbemectin, nitenpyram, oxamyl, permethrin, spinetoram, spinosad, spirodichlofen, spirotetramat, tefluthrin, thiacloprid, thiamethoxam, and thiodicarb. Suitable amounts of insecticides and nematicides for use according to the present disclosure are known in the art.

Non-limiting examples of commercial insecticides which can be suitable for the inoculants disclosed herein include, without limitation, CRUISER (Syngenta, Wilmington, Del.), GAUCHO and PONCHO (Gustafson, Plano, Tex.). Active ingredients in these and other commercial insecticides include, without limitation, thiamethoxam, clothianidin, and imidacloprid. Commercial insecticides are most suitably used in accordance with the manufacturer's instructions at the recommended concentrations.

Non-limiting examples of insecticides, acaricides, and nematicides that can be useful to the inoculants disclosed herein include, without limitation, carbamates, diamides, macrocyclic lactones, neonicotinoids, organophosphates, phenylpyrazoles, pyrethrins, spinosyns, synthetic pyrethroids, tetronic and tetramic acids.

In an aspect, insecticides, acaricides, and nematicides include, without limitation, acrinathrin, alpha-cypermethrin, betacyfluthrin, cyhalothrin, cypermethrin, deltamethrin csfenvalcrate, etofenprox, fenpropathrin, fenvalerate, flucythrinat, fosthiazate, lambda-cyhalothrin, gamma-cyhalothrin, permethrin, tau-fluvalinate, transfluthrin, zeta-cypermethrin, cyfluthrin, bifenthrin, tefluthrin, eflusilanat, fubfenprox, pyrethrin, resmethrin, imidacloprid, acetamiprid, thiamethoxam, nitenpyram, thiacloprid, dinotefuran, clothianidin, imidaclothiz, chlorfluazuron, diflubenzuron, lufenuron, teflubenzuron, triflumuron, novaluron, flufenoxuron, hexaflumuron, bistrifluoron, noviflumuron, buprofezin, cyromazine, methoxyfenozide, tebufenozide, halofenozide, chromafenozide, endosulfan, fipronil, ethiprole, pyrafluprole, pyriprole, flubendiamide, chlorantraniliprole (Rynaxypyr), chlothianidin, cyazypyr, emamectin, emamectin benzoate, abamectin, ivermectin, milbemectin, lepimectin, tebufenpyrad, fen pyroxi mate, pyridaben, fenazaquin, pyrimidifen, tolfenpyrad, dicofol, cyenopyrafen, cyflumetofen, acequinocyl, fluacrypyrin, bifenazate, diafenthiuron, etoxazole, clofentezine, spinosad, triarathen, tetradifon, propargite, hexythiazox, bromopropylate, chinomethionat, amitraz, pyrifluquinazon, pymetrozine, flonicamid, pyriproxyfen, diofenolan, chlorfenapyr, metaflumizone, indoxacarb, chlorpyrifos, spirodiclofen, spiromesifen, spirotetramat, pyridalyl, spinctoram, acephate, triazophos, profenofos, oxamyl, spinetoram, fenamiphos, fenamipclothiahos, 4-{[(6-chloropyrid-3-yl)methyl](2,2-difluoroethyl)amino}furan-2(5H)-one, cadusaphos, carbaryl, carbofuran, ethoprophos, thiodicarb, aldicarb, aldoxycarb, metamidophos, methiocarb, sulfoxaflor, cyantraniliprole, and also products based on *Bacillus firmus* (1-1582, BioNeem, VOTiVO™), and combinations thereof.

In another aspect, corn seeds are treated with a composition selected from the group consisting of cyantraniliprole, thiamethoxam, clothianidin, imidacloprid, sedaxane, azoxystrobin, fludioxonil, metalaxyl, mefenoxam, thiabenzole, prothioconazole, fluoxastrobin, fluxapyroxad, fluopyram, pyraclostrobin, VOTiVO™, a LCO, *Bradyrhizobium japonicum*, and combinations thereof.

Additional active components may also comprise substances such as biological control agents, microbial extracts, natural products, plant growth activators or plant defense agents. Non-limiting examples of biological control agents include bacteria, fungi, beneficial nematodes, and viruses.

In certain embodiments, the biological control agent can be a bacterium of the genus Actinomycetes, *Agrobacterium, Arthrobacter, Alcaligenes, Aureobacterium, Azobacter, Beijerinckia, Brevibacillus, Burkholderia, Chromobacterium, Clostridium, Clavibacter, Comomonas, Corynebacterium, Curtobacterium, Enterobacter, Flavobacterium, Gluconobacter, Hydrogenophage, Klebsiella, Methylobacterium, Paenibacillus, Pasteuria, Phingobacterium, Photorhabdus, Phyllobacterium, Pseudomonas, Rhizobium, Serratia, Stenotrophomonas, Streptomyces, Variovorax,* and *Xenorhadbus*. In particular embodiments the bacteria is selected from the group consisting of *Bacillus amyloliquefaciens, Bacillus cereus, Bacillus firmus, Bacillus lichenformis, Bacillus pumilus, Bacillus sphaericus, Bacillus subtilis, Bacillus thuringiensis, Bradyrhizobium japonicum, Chromobacterium suttsuga, Pasteuria nishizawae, Pasteuria penetrans, Pasteuria usage, Pseudomona fluorescens,* and *Streptomyces lydicus.*

In certain embodiments the biological control agent can be a fungus of the genus *Alternaria, Ampelomyces, Aspergillus, Aureobasidium, Beauveria, Colletotrichum, Coniothyrium, Gliocladium, Metarhisium, Muscodor, Paecilonyces, Penicillium, Trichoderma, Typhula, Ulocladium,* and *Verticilium*. In particular embodiments the fungus is *Beauveria bassiana, Coniothyrium minitans, Gliocladium virens, Metarhizium anisopliae, Muscodor albus, Paecilomyces lilacinus, Penicillium bilaii, Trichoderma polysporum,* and *Trichoderma virens.*

In further embodiments the biological control agents can be plant growth activators or plant defense agents including, but not limited to harpin, *Reynoutria sachalinensis*, jasmonate, lipochitooligosaccharides, and isoflavones.

In an aspect, the insecticide is a microbial insecticide. In a more particular aspect, the microbial insecticide is a fungal insecticide. Non-limiting examples of fungal insecticides that can be used in the compositions disclosed herein are described in McCoy, C. W., Samson, R A., and Coucias, D. G. "Entomogenous fungi." In "CRC Handbook of Natural Pesticides. Microbial Pesticides, Part A. Entomogenous Protozoa and Fungi." (C. M. Inoffo, ed.), (1988): Vol. 5, 151-236; Samson, R. A., Evans, H. C., and Latge, J. P. "Atlas of Entomopathogenic Fungi." (Springer-Verlag, Berlin) (1988); and deFaria, M. R. and Wraight, S. P. "Mycoinsecticides and Mycoacaricides: A comprehensive list with worldwide coverage and international classification of formulation types." Biol. Control (2007), doi: 10.1016/j.biocontrol.2007.08.001.

In an aspect, non-limiting examples fungal insecticides that can be used in the inoculants disclosed herein include, without limitation, species of *Coelomycidium, Myiophagus, Coelemomyces, Lagenidium, Leptolegnia, Couchia, Sporodiniella, Conidiobolus, Entomophaga, Entomophthora, Erynia, Massospora, Meristacrum, Neozygites, Pandora, Zoophthora, Blastodendrion, Metschnikowia, Mycoderma, Ascophaera, Cordyceps, Torrubiella, Nectria, Hypocrella, Calonectria, Filariomyces, Hesperomyces, Trenomyces, Myriangium, Podonectria, Akanthomyces, Aschersonia, Aspergillus, Beauveria, Culicinomyces, Engyodontium, Fusarium, Gibellula, Hirsutella, Hymenostilbe, Isaria, Metarhizium, Nomuraea, Paecilomyces, Paraisaria, Pleurodesmospora, Polycephalomyces, Pseudogibellula, Sorosporella, Stillbella, Tetranacrium, Tilachlidium, Tolypocladium, Verticillium, Aegerita, Filobasidiella, Septobasidium, Uredinella,* and combinations thereof.

Non-limiting examples of particular species that can be useful as a fungal insecticide in the inoculants described herein include, without limitation, *Trichoderma hamatum, Trichoderma hazarium, Alternaria cassiae, Fusarium lateritum, Fusarium solani, Lecanicillium lecanii, Aspergillus parasiticus, Verticillium lecanii, Metarhizium anisopliae,* and *Beauveria bassiana*. In an aspect, the inoculants disclosed herein can include any of the fungal insecticides provided above, including any combination thereof.

Fertilizer(s)

As used herein, "fertilizer(s)" is intended to mean any material of natural or synthetic origin that is applied to soils or to plant tissues to supply one or more plant nutrients essential to the growth of plants. Fertilizers can be utilized in an aspect of the present disclosure. In one aspect, a fertilizer can be used in combination with either an inoculant of the present disclosure or a part of a method of the present disclosure.

Commercially available manufactured phosphate fertilizers are of many types. Some common ones are those containing rock phosphate, monoammonium phosphate, diammonium phosphate, monocalcium phosphate, super phosphate, triple super phosphate, and/or ammonium polyphosphate. All of these fertilizers are produced by chemical processing of insoluble natural rock phosphates in large scale fertilizer-manufacturing facilities and the product is expensive. By means of the present disclosure, it is possible to reduce the amount of these fertilizers applied to the soil while still maintaining the same amount of phosphorus uptake from the soil.

An organic fertilizer refers to a soil amendment derived from natural sources that guarantees, at least, the minimum percentages of nitrogen, phosphate, and potash. Non-limiting examples of organic fertilizers include, without limitation, plant and animal by-products, rock powders, seaweed, compositions, and conditioners. These are often available at garden centers and through horticultural supply companies. In particular, the organic source of phosphorus is from bone meal, meat meal, animal manure, compost, sewage sludge, or guano, or combinations thereof.

Chitinous Compounds

As used herein, "chitinous compounds" are intended to mean chitins and chitosans, which are major components of the cell walls of fungi and the exoskeletons of insects and crustaceans, and are also composed of GlcNAc residues. In one aspect, a chitinous compound can be used in combination with, or be part of, either an inoculant of the present disclosure or a part of a method of the present disclosure.

Chitinous compounds include, without limitation, chitin, (IUPAC: N-[5-[[3-acetylamino-4,5-dihydroxy-6-(hydroxymethyl)oxan-2yl]methoxymethyl]-2-[[5-acetylamino-4,6-dihydroxy-2-(hydroxy methyl)oxan-3-yl]methoxymethyl]-4-hydroxy-6-(hydroxymethyl)oxan-3-ys] ethanamide), and chitosan, (IUPAC: 5-amino-6-[5-amino-6-[5-amino-4,6-dihydroxy-2(hydroxymethyl)oxan-3-yl]oxy-4-hydroxy-2-(hydroxymethyl)oxan-3-yl]oxy-2 (hydroxymethyl)oxane-3,4-diol). These compounds can be obtained commercially, e.g., from Sigma-Aldrich, or prepared from insects, crustacean shells, or fungal cell walls. Methods for the preparation of chitin and chitosan are known in the art, and have been described, for example, in U.S. Pat. No. 4,536,207 (preparation from crustacean shells), Pochanavanich, et al., Lett. Appl. Microbiol. 35:17-21 (2002) (preparation from fungal cell walls), and U.S. Pat. No. 5,965,545 (preparation from crab shells and hydrolysis of commercial chitosan). Deacetylated chitins and chitosans can be obtained that range from less than 35% to greater than 90% deacetylation, and cover a broad spectrum of molecular weights, e.g., low molecular weight chitosan oligomers of less than 15 kD and chitin oligomers of 0.5 to 2 kD; "practical grade" chitosan with a molecular weight of about 15 kD; and high molecular weight chitosan of up to 70 kD. Chitin and chitosan compositions formulated for seed treatment are also commercially available. Commercial products include, without limitation, for example, ELEXA® (Plant Defense Boosters, Inc.) and BEYOND™ (Agrihouse, Inc.). Chitinous compounds can be utilized in an aspect of the present disclosure.

Flavonoids/Jasmonic Acid/Linolenic Acid

In one aspect, a flavonoid, jasmonic acid or linolenic acid can be used in combination with, or be part of, either an inoculant of the present disclosure or part of a method of the present disclosure. Flavonoids are phenolic compounds having the general structure of two aromatic rings connected by a three-carbon bridge.

Classes of flavonoids include, without limitation, chalcones, anthocyanidins, coumarins, flavones, flavanols, flavonols, flavanones, and isoflavones. See, Jain, et al., J. Plant Biochem. & Biotechnol. 77:1-10 (2002); Shaw, et al., Environmental Microbiol. 77:1867-80 (2006).

As used herein, the term "isoflavonoids" means phytoestrogens, isoflavones (e.g., genistein, daidzein, glycitein, etc.), and isoflavanes (e.g., equol, lonchocarpane, laxiflorane, etc.). Isoflavonoids can be utilized in an aspect of the present disclosure. In one aspect, isoflavonoids can be used in combination with, or be part of, either an inoculant of the present disclosure or a part of a method of the present disclosure.

Representative flavonoids that can be useful in the practice of the present disclosure include, without limitation, genistein, daidzein, formononetin, naringenin, hesperetin, luteolin, and apigenin. Jasmonic acid (JA, [1 R-[1 a,2 (Z)]]-3-oxo-2-(pentenyl)cyclopentaneacetic acid) and its derivatives, linoleic acid ((Z,Z)-9,12-Octadecadienoic acid) and its derivatives, and linolenic acid ((Z,Z,Z)-9,12,15-octadecatrienoic acid) and its derivatives, can be used in the practice of the present disclosure. Jasmonic acid and its methyl ester, methyl jasmonate (MeJA), collectively known as jasmonates, are octadecanoid-based compounds that occur naturally in plants. Jasmonic acid may be produced by the roots of wheat seedlings, and by fungal microorganisms such as Botryodiplodia theobromae and Gibberella fujjikuroi, yeast (Saccharomyces cerevisiae), and pathogenic and non-pathogenic strains of Escherichia coli. Jasmonates, linoleic acid and linoleic acid (and their derivatives) are reported to be inducers of nod gene expression or LCO production by rhizobacteria. See, e.g., Mabood, Fazli, "Jasmonates induce the expression of nod genes in Bradyrhizobium japonicum," May 17, 2001; and Mabood, Fazli, "Linoleic and linolenic acid induce the expression of nod genes in Bradyrhizobium japonicum," USDA 3, May 17, 2001.

Useful derivatives of linoleic acid, linolenic acid, and jasmonic acid that can be useful in the practice of the methods herein include, without limitation, esters, amides, glycosides and salts. Representative esters are compounds in which the carboxyl group of linoleic acid, linolenic acid, orjasmonic acid has been replaced with a —COR group, where R is an —OR$^1$ group, in which R$^1$ is: an alkyl group, such as a C$_1$-C$_8$ unbranched or branched alkyl group, e.g., a methyl, ethyl or propyl group; an alkenyl group, such as a C$_2$-C$_8$ unbranched or branched alkenyl group; an alkynyl group, such as a C$_2$-C$_8$ unbranched or branched alkynyl group; an aryl group having, for example, 6 to 10 carbon atoms; or a heteroaryl group having, for example, 4 to 9 carbon atoms, wherein the heteroatoms in the heteroaryl group can be, for example, N, O, P, or S. Representative amides are compounds in which the carboxyl group of linoleic acid, linolenic acid, or jasmonic acid has been replaced with a —COR group, where R is an NR$^2$R$^3$ group, in which R$^2$ and R$^3$ are independently hydrogen; an alkyl group, such as a C$_1$-C$_8$ unbranched or branched alkyl group, e.g., a methyl, ethyl or propyl group; an alkenyl group, such as a C$_2$-C$_8$ unbranched or branched alkenyl group; an alkynyl group, such as a C$_2$-C$_8$ unbranched or branched alkynyl group; an aryl group having, for example, 6 to 10 carbon atoms; or a heteroaryl group having, for example, 4 to 9 carbon atoms, wherein the heteroatoms in the heteroaryl group can be, for example, N, O, P, or S. Esters can be prepared by known methods, such as acid-catalyzed nucleophilic addition, wherein the carboxylic acid is reacted with an alcohol in the presence of a catalytic amount of a mineral acid. Amides can also be prepared by known methods, such as by reacting the carboxylic acid with the appropriate amine in the presence of a coupling agent such as dicyclohexyl carbodiimide (DCC), under neutral conditions. Suitable salts of linoleic acid, linolenic acid, and jasmonic acid include, without limitation, e.g., base addition salts. The bases that can be used as reagents to prepare metabolically acceptable base salts of these compounds include those derived from cations such as alkali metal cations (e.g., potassium and sodium) and alkaline earth metal cations (e.g., calcium and magnesium). These salts can be readily prepared by mixing together a solution of linoleic acid, linolenic acid, or jasmonic acid with a solution of the base. The salt can be precipitated from solution and be collected by filtration or can be recovered by other means such as by evaporation of the solvent.

Karikins

Karrikins are vinylogous 4H-pyrones e.g., 2H-furo[2,3-c]pyran-2-ones. In one aspect, an Karrikins can be used in combination with, or be part of, either an inoculant of the present disclosure or a part of a method of the present disclosure. In one aspect, Karrikins include, without limitation, derivatives and analogues thereof. Examples of these compounds are represented by the following structure:

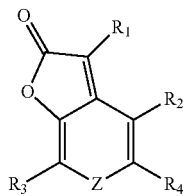

wherein; Z is O, S or $NR_5$; $R_1$, $R_2$, $R_3$, and $R_4$ are each independently H, alkyl, alkenyl, alkynyl, phenyl, benzyl, hydroxy, hydroxyalkyl, alkoxy, phenyloxy, benzyloxy, CN, $COR_6$, COOR=, halogen, $NR_6R_7$, or $NO_2$; and $R_5$, $R_6$, and $R_7$ are each independently H, alkyl or alkenyl, or a biologically acceptable salt thereof. Examples of biologically acceptable salts of these compounds can include, without limitation, acid addition salts formed with biologically acceptable acids, examples of which include, without limitation, hydrochloride, hydrobromide, sulphate or bisulphate, phosphate or hydrogen phosphate, acetate, benzoate, succinate, fumarate, maleate, lactate, citrate, tartrate, gluconate; methanesulphonate, benzenesulphonate and p-toluenesulphonic acid. Additional biologically acceptable metal salts can include, without limitation, alkali metal salts, with bases, examples of which include the sodium and potassium salts. Examples of compounds embraced by the structure and which can be suitable for use in the present disclosure include, without limitation, the following: 3-methyl-2H-furo[2,3-c]pyran-2-one (where $R_1$=$CH_3$, $R_2$, $R_3$, $R_4$=H), 2H-furo[2,3-c]pyran-2-one (where $R_1$, $R_2$, $R_3$, $R_4$=H), 7-methyl-2H-furo[2,3-c]pyran-2-one (where $R_1$, $R_2$, $R_4$=H, $R_3$=$CH_3$), 5-methyl-2H-furo[2,3-c]pyran-2-one (where $R_1$, $R_2$, $R_3$=H, $R_4$=$CH_3$), 3,7-dimethyl-2H-furo[2,3-c]pyran-2-one (where $R_1$, $R_3$=$CH_3$, $R_2$, $R_4$=H), 3,5-dimethyl-2H-furo[2,3-c]pyran-2-one (where $R_1$, $R_4$=$CH_3$, $R_2$, $R_3$=H), 3,5,7-trinnethyl-2H-furo[2,3-c]pyran-2-one (where $R_1$, $R_3$, $R_4$=$CH_3$, $R_2$=H), 5-methoxynnethyl-3-nnethyl-2H-furo[2,3-c]pyran-2-one (where $R_1$=CH3, $R_2$, $R_3$=H, $R_4$=$CH_2OCH_3$), 4-bromo-3,7-dimethyl-2H-furo[2,3-c]pyran-2-one (where $R_1$, $R_3$=$CH_3$, $R_2$=Br, $R_4$=H), 3-methylfuro[2,3-c]pyridin-2(3H)-one (where Z=NH, $R_1$=$CH_3$, $R_2$, $R_3$, $R_4$=H), 3,6-dimethylfuro[2,3-c]pyridin-2(6H)-one (where Z=N—$CH_3$, $R_1$=$CH_3$, $R_2$, $R_3$, $R_4$=H). See, U.S. Pat. No. 7,576,213. These molecules are also known as Karrikins. See, Halford, supra. Karrikins can be utilized in an aspect of the present disclosure.

Methods

In one aspect, the present disclosure provides growing an inoculated corn plant or corn seed in soil after one or more consecutive corn plantings in the soil where the inoculant is capable of reducing a corn-on-corn yield penalty.

In one aspect the soil is present in a field. A field can be any field. In one aspect, an area of land, enclosed or otherwise, is used for agricultural purposes such as cultivating crops. In one aspect, a field or area of land/soil for growing corn is greater than 100 square meters, 500 square meters, 1 acre, 5 acres, 10 acres, 20 acres, or 50 acres.

In one aspect, a consecutive corn planting is any continuous corn planting in which a first corn planting in an earlier growing season is followed by a second corn planting in a later growing season and not interrupted by a non-corn planting. In one aspect, a non-corn can be a nitrogen-fixing plant, the nitrogen-fixing plant may or may not be a leguminous plant, and the leguminous plant may or may not be a soybean plant. In addition, the non-corn may be a non-nitrogen fixing plant, including but not limited to, wheat and cotton.

In one aspect, consecutive corn planting(s) may be 2, 3, 4, 5 or 6 or more consecutive corn plantings without an intervening non-corn rotation.

In one aspect, a planting can be a consecutive non-nitrogen fixing planting.

In one aspect, consecutive non-nitrogen fixing plant planting is any continuous non-nitrogen fixing plant planting in which an earlier non-nitrogen fixing plant planting in an earlier growing season is followed by a later non-nitrogen fixing plant planting in a later growing season and not interrupted by a nitrogen fixing plant planting.

As used herein, the term "corn-on-corn" is intended to mean corn plantings in two or more consecutive growing seasons in the same fields and not rotated with a non-corn crop.

In one aspect, a method or inoculant results in the reduction of a corn-on-corn yield penalty. As used herein, the term "corn-on-corn yield penalty" (CCYP) is defined as follows:

$$CCYP = Y_{NC} - Y_{CC}$$

in which, $Y_{NC}$ is the yield of corn in a later growing season following an immediate prior planting of a non-corn (NC) plant in an earlier growing season, where the non-corn may be a nitrogen-fixing plant, the nitrogen-fixing plant may or may not be a leguminous plant, and the leguminous plant may or may not be a soybean plant. In addition, the non-corn may be a non-nitrogen fixing plant, including but not limited to, wheat and cotton; and $Y_{CC}$ is the yield of corn in a later growing season following an immediate prior planting of corn in an earlier growing season. In one aspect, CCYP is measured as set forth in Example 2.

In one aspect, the reduction of a corn-on-corn yield penalty is more than 3%, 5%, 10%, 15%, or 20% of an untreated corn seed or plant. In one aspect, corn-on-corn yield penalty is measured on a single plant. In other aspects, a corn-on-corn yield penalty is measured on a group of plants where the group of plants is greater than 100, 200, 500, or 1000 corn plants. In one aspect, CCYP reduction is a capability of a provided inoculant or method.

In an aspect, the inoculant is applied to the corn seeds prior to planting. In an aspect, the applying is at least 0.25, 0.5, 0.75, 1, 2, 3, 4, 5, 6, 7, 8, 9, 10, 11, 12, 15, 18, 21, 24, 27, 30, 33, 36 months or more prior to planting. In an aspect, corn was sown in the soil for at least the previous two or more consecutive growing seasons. In an aspect, the at least previous two or more growing seasons is the previous three, four, five, six, seven, eight, nine, ten or more growing seasons. In an aspect, the method is capable of reducing the corn-on-corn yield penalty from consecutive corn planting by at least about 5, 10, 15, 20, 25, 30, 35, 40, 45, 50, 55, 60, 65, 70, 75, 80, 85, 90, 95% or more. In an aspect, the corn-on-corn yield penalty is less than 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, or 50 bushels/acre.

In one aspect, "applying" or "applied" can be performed by any person but, without limitation, can be performed in its entirety by a farmer, a farm worker, a laborer, a seed distributor, an agrochemical company, an agricultural technology company, or any other parties similarly situated.

In one aspect, the present disclosure includes a method of crop rotation management that provides for two consecutive corn plantings in a field where the later planting provides a yield that is at least 80%, 82%, 84%, 86%, 88%, 90%, 92%, 94%, 96%, 98%, 100%, 102%, 104%, 106%, 108%, 110%, 115%, 120%, or 125% of the yield of the earlier planting, the method comprising: a) treating corn seeds with an inoculant comprising an effective amount of *Penicillium bilaii*; and b) providing the treated corn seeds to a farmer for growing in a field in which corn was planted in an immediately preceding growing season.

In an aspect, an effective amount of the composition containing *Penicillium bilaii* is present in an amount from about 8 to about 16 ounce/acre. In an aspect, the effective amount of the composition containing *Penicillium bilaii* is at a concentration of at least about 8 ounce/acre, at least about 9 ounce/acre, at least about 10 ounce/acre, at least about 11 ounce/acre, at least about 12 ounce/acre, at least about 13 ounce/acre, at least about 14 ounce/acre, at least about 15 ounce/acre, or at least about 16 ounce/acre. In an aspect, the effective amount of the composition containing *Penicillium bilaii* is at a concentration from about 8 to about 16 ounce/acre, from about 9 to about 16 ounce/acre, from about 10 to about 16 ounce/acre, from about 11 to about 16 ounce/acre, from about 12 to about 16 ounce/acre, from about 13 to about 16 ounce/acre, from about 14 to about 16 ounce/acre, or from about 15 to about 16 ounce/acre. In another aspect, the *Penicillium bilaii* inoculant can range from about $1 \times 10^6$ to about $1 \times 10^8$ cfu per pound of seeds. In one aspect, the *Penicillium bilaii* inoculant is present in an amount of about $1.7 \times 10^7$ cfu per pound of seeds.

In an aspect, the yield of corn grown in the field with the inoculant is at least 3%, 4%, 5%, 6%, 7%, 8%, 9%, 10%, 11%, 12%, 13%, 14%, or 15% higher than the yield of corn grown in a comparable field after one or more consecutive corn plantings without the inoculant.

In an aspect, the yield of corn grown in the field with the inoculant is from about 0.5% to about 15%, 1% to about 15%, 2% to about 15%, 3% to about 15%, from about 4% to about 15%, from about 5% to about 15%, from about 6% to about 15%, from about 7% to about 15%, from about 8% to about 15%, from about 9% to about 15%, from about 10% to about 15%, from about 11% to about 15%, from about 12% to about 15%, from about 13% to about 15%, or from about 14% to about 15% higher than the yield of corn grown in a comparable field after one or more consecutive corn plantings without the inoculant.

In an aspect, the present disclosure includes a method comprising providing to a person a population of corn seeds in need of reducing a corn-on-corn yield penalty and an inoculant comprising an effective amount of *Penicillium bilaii*, where the amount is effective for reducing the corn-on-corn yield penalty.

As used herein, the term "a person" is intended to mean a farmer, a farm worker, a laborer, or any other parties similarly situated. In one aspect, a method can be carried out by a person in need thereof.

In yet another aspect, the present disclosure includes a method for growing a population of corn plants, comprising selecting a field in which corn was grown during a growing season that immediately precedes selection of the field, planting corn seeds in need of reducing a corn-on-corn yield penalty treated with an inoculant comprising an effective amount of *Penicillium bilaii* in the selected field, where the amount is effective for reducing the corn-on-corn yield penalty.

As used herein, the term "growing season(s)" is intended to mean a period of time in a given year when the climate is prime for crops to experience the most growth.

As used herein, the terms "first," "second," "previous," "prior," "earlier," "later," or "subsequent" refer to a temporal relationship between two plantings of a population of plants immediately after one another in two consecutive growing seasons without being interrupted by a third planting of a population of plants.

An aspect of the present disclosure includes a method of preventing or reducing a corn-on-corn yield penalty in a population of corn plants in need thereof comprising: a) applying an inoculant comprising an effective amount of *Penicillium bilaii* to corn seeds and/or to a field in which corn was grown during a growing season that immediately precedes planting; and b) planting the corn seeds in the field without growing a population of non-corn plants in the field prior to planting the corn seeds, where the amount is effective to prevent or reduce the corn-on-corn yield penalty.

In an aspect, the field in which corn was grown during a growing season that immediately precedes planting of the corn seeds did not grow a population of non-corn plants in any of the two growing seasons that immediately preceded planting of the corn seeds. In another aspect, the population of non-corn plants is planted at least 10,000 plants/acre. In an aspect, the field in which corn was grown during a growing season that immediately precedes planting of the corn seeds was not fallow in any of the two or more growing seasons that immediately preceded planting of the corn seeds. In an aspect, the population of non-corn plants are nitrogen-fixing plants. In an aspect, the nitrogen-fixing plants are leguminous plants. In an aspect, the leguminous plants are soybean plants. In an aspect, the population of non-corn plants are non-nitrogen-fixing plants. In an aspect, the non-nitrogen-fixing plants are selected from the group consisting of wheat and cotton. In an aspect, the yield of the population of corn plants is equal to or greater than the corn yield of a comparable field without the inoculant. In a further aspect, the yield of the population of corn plants is equal to or greater than the corn yield of a comparable field without the inoculant.

As used herein, the term "comparable field" is intended to mean a field in an approximate location to the field applied with the inoculant, grown in essentially similar soil and weather conditions as the field applied with the inoculant, and planted with similar corn seeds under the same management (i.e., corn plants were grown the previous growing season) and treatments as the field applied with the inoculant.

A further aspect of the present disclosure is that the disclosure includes a method of enhancing corn yield in a field grown in a corn-on-corn rotation for two or more consecutive growing seasons, comprising: a) growing a first population of corn plants in the field during a first growing season; and b) growing a second population of corn plants in the field during a second growing season, where the second population of corn plants is treated with an inoculant comprising *Penicillium bilaii* prior to planting, at the time of planting and/or after planting, and where the first and second growing seasons are consecutive growing seasons.

In an aspect, the inoculant is applied to the corn seeds of the second population of corn plants prior to planting. In an aspect, the inoculant is applied to the soil prior to planting. In an aspect, the inoculant is applied to the seeds of the second population of corn plants at planting. In an aspect, the inoculant is applied to the soil after planting. In an aspect, the inoculant is applied to the foliage of the second population of corn plants. In an aspect, the population of non-corn plants are nitrogen-fixing plants. In an aspect, the field was not fallow in the two or more consecutive corn growing seasons. In one aspect, the yield of the second population of corn plants is equal to or more than the yield of the first population of corn plants.

As used herein, the terms "crop rotation" and "rotation" are intended to mean the planting of one or more different crops in the same field in consecutive growing seasons, in contrast to a one-crop system or to haphazard crop successions.

In an aspect, the non-corn plants are nitrogen-fixing plant. In an aspect, the nitrogen-fixing plants are leguminous plants. In an aspect, the leguminous plants are soybean plants. In an aspect, the non-corn plants are non-nitrogen-fixing plant. In an aspect, the non-nitrogen-fixing plants are selected from the group consisting of wheat and cotton.

In an aspect, the method further comprises growing a third corn crop in the field in a third subsequent growing season where the yield of the third population of corn plants is at least equal to the first or second population of corn plants.

In another aspect, the disclosure includes a method of reducing a corn-on-corn yield penalty in a field grown in a corn-on-corn rotation for two or more consecutive growing seasons, comprising: a) growing a first population of corn plants in the field during a first growing season; and b) growing a second population of corn plants in the field during a second growing season; the second population of corn plants is treated with an inoculant comprising *Penicillium bilaii* prior to planting, at the time of planting and/or after planting, and where the first and second growing seasons are consecutive growing seasons.

An even further aspect of the present disclosure includes a method of crop rotation management that provides for two consecutive corn plantings in a field where the later planting provides a yield that is at least 80%, 82%, 84%, 86%, 88%, 90%, 92%, 94%, 96%, 98%, 100%, 102%, 104%, 106%, 108%, 110%, 115%, 120%, or 125% of the yield of the earlier planting, the method comprising: a) treating corn seeds with an inoculant comprising an effective amount of *Penicillium bilaii*; and b) providing the treated corn seeds to a farmer for growing in a field in which corn was planted in an immediately preceding growing season.

Treating can be performed in its entirety by any appropriate entity, including without limitation, a farmer, a farm worker, a laborer, a seed distributor, an agrochemical company, an agricultural technology company, or any other parties similarly situated.

In an aspect, the field has not been intercropped in any one of the previous two, three, four, or five consecutive growing seasons. In an aspect, a population of nitrogen-fixing plants is not grown in any one of the previous two, three, four, or five consecutive growing seasons. In an aspect, the nitrogen-fixing plants are leguminous plants. In an aspect, the leguminous plants are soybean plants.

The present disclosure further includes a method of reducing a corn-on-corn yield penalty, the method comprising: a) planting corn seeds in need thereof that have been treated with an inoculant comprising *Penicillium bilaii* in a field in which corn was grown during a growing season that immediately precedes planting of the corn seeds in need thereof; b) growing corn from the corn seeds in need thereof; and c) producing a yield of corn where the corn-on-corn yield penalty is reduced as a result of the inoculant comprising *Penicillium bilaii*.

In an aspect, the yield of corn from the corn seeds in need thereof is greater than the yield of corn obtained from the corn field in the prior growing season that immediately precedes planting of the corn seeds in need thereof.

In another aspect, the present disclosure includes a method of reducing the corn-on-corn yield penalty, the method comprising: a) administering, to a population of corn plants, corn seeds, and/or soil containing a population of corn plants or corn seeds in need thereof, an inoculant comprising an effective amount of *Penicillium bilaii*; and b) growing the population of corn plants or corn seeds in need thereof in the soil; where corn was grown in the soil during a growing season that immediately precedes growth of the population of corn plant or corn seeds.

As used herein, the term "administering" could be performed in its entirety by a farmer, a farm worker, a laborer, a seed distributor, an agrochemical company, an agricultural technology company, or any other parties similarly situated.

In yet another aspect, the present disclosure further includes a method comprising: a) planting corn seeds in soil in which corn was grown during a growing season that immediately precedes planting of the corn seeds; and b) applying an inoculant comprising *Penicillium bilaii* to the soil, to the corn seeds and/or to plants that germinate from the corn seeds, where the inoculant is capable of increasing the yield of the plants.

In an aspect, no seeds of a non-corn plant were sown in the soil during any one of the previous 1, 2, 3, 4, 5, 6, 7, 8, 9, 10 or more growing seasons. In an aspect, the method further comprises applying one or more compositions selected from the group consisting of one or more agronomically beneficial elements to the soil, one or more agronomically beneficial elements to the seed, one or more agronomically beneficial elements to the plant that germinates from the seed, one or more lipo-chitooligosaccharides, one or more chitooligosaccharides, one or more chitinous compounds, one or more isoflavonoids, jasmonic acid or derivatives thereof, linolenic acid or derivatives thereof, linoleic acid or derivatives thereof, one or more karrakins, one or more pesticides, one or more fertilizers, and any combination of the above inoculants.

The present disclosure further includes a method of maximizing a field's farming revenue, the method comprising: a) determining a first projected net revenue from consecutive plantings of corn for at least two growing seasons in the field; b) determining a second projected net revenue from a corn on non-corn rotation in the field for the same number of growing seasons; c) determining a third projected net revenue from consecutive plantings of corn for at least two growing seasons in the field, where the third projected net revenue assumes that the corn and/or the field will be treated with an inoculant capable of reducing a corn-on-corn yield penalty in the field; d) comparing the first, second and third projected net revenues; e) recommending consecutive corn plantings; and f) providing corn seeds that have been treated with an inoculant comprising an effective amount of *Penicillium bilaii*.

The present disclosure also includes a method comprising a) providing a farmer in need thereof with instructions for reducing a corn-on-corn yield penalty by applying an effective amount of an inoculant comprising *Penicillium bilaii* to a corn seed or to plants growing from the corn seed; and b) providing to the farmer with the inoculant.

Although the disclosure herein has been described with reference to particular aspects, it is to be understood that these aspects are merely illustrative of the principles and applications of the present disclosure. It is therefore to be understood that numerous modifications may be made to the illustrative aspects and that other arrangements may be devised without departing from the spirit and scope of the present disclosure as defined by the appended claims.

The following are exemplary embodiments of the present disclosure.

Embodiment 1

A method comprising:
a. applying an inoculant comprising *Penicillium bilaii* to a population of corn plants or corn seeds in need of reducing a corn-on-corn yield penalty; and
b. growing or planting said population of corn plants or corn seeds in need thereof in a field in which corn was grown during a growing season that immediately precedes planting of said population of corn plants or corn seeds in need thereof, wherein said inoculant is capable of reducing said corn-on-corn yield penalty.

Embodiment 2

The method of Embodiment 1, wherein said *Penicillium bilaii* is at least 75% identical to a deposited strain on the basis of 16S rDNA sequence identity, wherein said deposited strain is selected from the group consisting of ATCC 20851, NRRL 50169, ATCC 22348, ATCC 18309, NRRL 50162, NRRL 50776, NRRL 50777, NRRL 50778, NRRL 50779, NRRL 50780, NRRL 50781, NRRL 50782, NRRL 50783, NRRL 50784, NRRL 50785, NRRL 50786, NRRL 50787, NRRL 50788, RS7B-SD1, and combinations thereof.

Embodiment 3

The method of Embodiments 1 or 2, wherein said *Penicillium bilaii* strains are NRRL 50169 and NRRL 50162.

Embodiment 4

The method of any one of Embodiments 1 to 3, wherein a source of phosphorus is added to soil of said field.

Embodiment 5

The method of any one of Embodiments 1 to 4, wherein said source is rock phosphate.

Embodiment 6

The method of any one of Embodiments 1 to 5, wherein said source is a manufactured fertilizer.

Embodiment 7

The method of any one of Embodiments 1 to 6, wherein said manufactured fertilizer is selected from the group consisting of monoammonium phosphate, triple super phosphate, diammonium phosphate, ordinary superphosphate, and ammonium polyphosphate.

Embodiment 8

The method of any one of Embodiments 1 to 4, wherein said phosphorus source is organic.

Embodiment 9

The method of Embodiment 8, wherein said organic source of phosphorus comprises bone meal, meat meal, animal manure, compost, sewage sludge, guano, and mixtures thereof.

Embodiment 10

The method of any one of Embodiments 1 to 9, wherein said inoculant further comprises a *Penicillium* fungus selected from the group consisting of *P. albidum, P. aurantiogriseum, P. chrysogenum P. citreonigrum P. citrinum P. digitatum, P. frequentas, P. fuscum, P. gaestrivorus, P. glabrum, P. griseofulvum, P. implicatum, P. janthinellum, P. lilacinum, P. minioluteum, P. montanense, P. nigricans, P. oxalicum, P. pinetorum, P. pinophilum, P. purpurogenum, P. radicans, P. radicum, P. raistrickii, P. rugulosum, P. simplicissimum, P. solitum, P. variabile, P. velutinum, P. viridicatum P. glaucum P. fussiporus*, and *P. expansum*.

Embodiment 11

The method of any one of Embodiments 1 to 10, wherein said inoculant further comprises an agronomically acceptable carrier.

Embodiment 12

The method of any one of Embodiments 1 to 11, wherein said inoculant is present in an amount from $10^6$ to $10^{11}$ colony forming units per hectare.

Embodiment 13

The method of any one of Embodiments 1 to 12, wherein said inoculant is present in an amount from $10^{-9}$ μg/seed to 1 μg/seed.

Embodiment 14

The method of any one of Embodiments 1 to 13, wherein said inoculant is provided in an amount from about 8 to about 16 ounce/acre.

Embodiment 15

The method of any one of Embodiments 1 to 14, wherein said inoculant is provided in an amount from about $1\times10^6$ to about $1\times10^8$ cfu per pound of corn seeds.

Embodiment 16

The method of any one of Embodiments 1 to 15, wherein a yield of corn grown in said field with said inoculant is at least 3%, 4%, 5%, 6%, 7%, 8%, 9%, 10%, 11%, 12%, 13%, 14%, or 15% higher than a yield of corn grown in a comparable field after one or more consecutive corn plantings without said inoculant.

Embodiment 17

The method of any one of Embodiments 1 to 16, wherein said applying said inoculant is selected from the group consisting of coating said corn seeds with said inoculant prior to planting, applying said inoculant to soil of said field prior to planting, applying said inoculant to soil of said field at planting, applying said inoculant to soil of said field after planting, and applying said inoculant to foliage of said population of corn plants growing in said field.

Embodiment 18

The method of any one of Embodiments 1 to 17, wherein said applying is applying said inoculant in-furrow.

Embodiment 19

The method of any one of Embodiments 1 to 18, wherein said applying is applying said inoculant to said corn seeds as a seed coating.

Embodiment 20

The method of any one of Embodiments 1 to 19, wherein said applying is coating said corn seeds with a seed coating comprising $10^1$-$10^8$ colony forming units of said *Penicillium bilaii* per seed.

Embodiment 21

The method of Embodiment 20, wherein said seed coating comprises $10^2$-$10^6$ colony forming units of said *Penicillium bilaii* per seed.

Embodiment 22

The method of any one of Embodiments 1 to 21, wherein said population of corn plants or corn seeds are further treated with a fertilizer.

Embodiment 23

A method comprising providing to a person a population of corn seeds in need of reducing a corn-on-corn yield penalty and an inoculant comprising an effective amount of *Penicillium bilaii*, wherein said amount is effective for reducing said corn-on-corn yield penalty.

Embodiment 24

The method of Embodiment 23, wherein said inoculant is applied to said corn seeds prior to said providing.

Embodiment 25

The method of Embodiments 23 or 24, wherein said inoculant is applied to said corn seeds prior to planting.

Embodiment 26

The method of any one of Embodiments 23 to 25, wherein said inoculant is applied to soil in which said population of corn seeds is growing prior to planting.

Embodiment 27

The method of any one of Embodiments 23 to 26, wherein said inoculant is applied to said corn seeds at planting.

Embodiment 28

The method of any one of Embodiments 23 to 27, wherein said inoculant is applied to soil in which said population of corn seeds is growing prior to development stage V1.

Embodiment 29

The method of any one of Embodiments 23 to 28, wherein said inoculant is applied to foliage of corn plants germinating from said corn seeds prior to development stage V1.

Embodiment 30

The method of any one of Embodiments 23 to 29, wherein a field in which said population of corn seeds is growing is greater than 100 square meters.

Embodiment 31

A method for growing a population of corn plants, comprising selecting a field in which corn was grown during a growing season that immediately precedes selection of said field, planting corn seeds in need of reducing a corn-on-corn yield penalty treated with an inoculant comprising an effective amount of *Penicillium bilaii* in said selected field, wherein said amount is effective for reducing said corn-on-corn yield penalty.

Embodiment 32

The method of Embodiment 31, wherein said inoculant further comprises an agronomically acceptable carrier.

Embodiment 33

The method of Embodiments 31 or 32, wherein said inoculant further comprises a pesticide.

Embodiment 34

The method of any one of Embodiments 31 to 33, wherein said pesticide is selected from the group consisting of an insecticide, a fungicide, a nematicide, and combinations thereof.

Embodiment 35

The method of any one of Embodiments 31 to 34, wherein said treating with said *Penicillium bilaii* is selected from the group consisting of coating said corn seeds prior to planting, applying to soil of said field prior to planting, applying to soil of said field at planting, applying to soil of said field after planting, and applying to foliage of a population of corn plants growing in said field.

Embodiment 36

A method of preventing a corn-on-corn yield penalty in a population of corn plants in need thereof comprising:
  a. applying an inoculant comprising an effective amount of *Penicillium bilaii* to corn seeds and/or to a field in which corn was grown during a growing season that immediately precedes planting; and
  b. planting said corn seeds in said field without growing a population of non-corn plants in said field prior to planting said corn seeds, wherein said amount is effective to prevent said corn-on-corn yield penalty.

Embodiment 37

A method of reducing a corn-on-corn yield penalty in a population of corn plants in need thereof comprising:
  a. applying an inoculant comprising an effective amount of *Penicillium bilaii* to corn seeds and/or to a field in which corn was grown during a growing season that immediately precedes planting of said corn seeds; and
  b. planting said corn seeds in said field without growing a population of non-corn plants in said field prior to planting said corn seeds, wherein said amount is effective to reduce said corn-on-corn yield penalty.

Embodiment 38

The method of Embodiment 36, wherein said field in which corn was grown during a growing season that immediately precedes planting of said corn seeds did not grow a population of non-corn plants in any of the two growing seasons that immediately preceded planting of said corn seeds.

Embodiment 39

The method of Embodiment 37, wherein said field in which corn was grown during a growing season that immediately precedes planting of said corn seeds did not grow a population of non-corn plants in any of the two growing seasons that immediately preceded planting of said corn seeds.

Embodiment 40

The method of Embodiments 36 or 38 wherein said population of non-corn plants is planted at least 10,000 plants/acre.

Embodiment 41

The method of any one of Embodiments 36, 38, or 40 wherein said field in which corn was grown during a growing season that immediately precedes planting of said corn seeds was not fallow in any of the two growing seasons that 30 immediately preceded planting of said corn seeds.

Embodiment 42

The method of Embodiments 37 or 39, wherein said field in which corn was grown during a growing season that immediately precedes planting of said corn seeds was not fallow in any of the two growing seasons that immediately preceded planting of said corn seeds.

Embodiment 43

The method of any one of Embodiments 36, 38, 40, or 41 wherein said population of non-corn plants are nitrogen-fixing plants.

Embodiment 44

The method of any one of Embodiments 36, 38, 40, 41, or 43, wherein said nitrogen-fixing plants are leguminous plants.

Embodiment 45

The method of any one of Embodiments 36, 38, 40, 41, 43, or 44, wherein said leguminous plants are soybean plants.

Embodiment 46

The method of Embodiment 38, wherein said population of non-corn plants are non-nitrogen-fixing plants.

Embodiment 47

The method of Embodiment 46, wherein said non-nitrogen-fixing plants are selected from the group consisting of wheat and cotton.

Embodiment 48

The method of any one of Embodiments 36, 38, 40, 41, 43, 44 or 45, wherein a yield of said population of corn plants is equal to or greater than a corn yield of a comparable field without said inoculant.

Embodiment 49

The method of any one of Embodiments 37, 39, or 42, wherein a yield of said population of corn plants is equal to or greater than a corn yield of a comparable field without said inoculant.

Embodiment 50

A method of enhancing corn yield in a field grown in a corn-on-corn rotation for two or more consecutive growing seasons, comprising:
  a. growing a first population of corn plants in said field during a first growing season; and b. growing a second population of corn plants in said field during a second growing season, wherein said second population of corn plants is treated with an inoculant comprising *Penicillium bilaii* prior to planting, at the time of planting and/or after planting, and wherein said first and second growing seasons are consecutive growing seasons.

Embodiment 51

The method of Embodiment 50, wherein said inoculant is applied to seeds of said second population of corn plants prior to planting.

Embodiment 52

The method of Embodiments 50 or 51, wherein said inoculant is applied to soil of said field prior to planting.

Embodiment 53

The method of any one of Embodiments 50 to 52, wherein said inoculant is applied to seeds of said second population of corn plants at planting.

Embodiment 54

The method of any one of Embodiments 50 to 53, wherein said inoculant is applied to soil of said field after planting.

Embodiment 55

The method of any one of Embodiments 50 to 54, wherein said inoculant is applied to foliage of said second population of corn plants.

Embodiment 56

The method of any one of Embodiments 50 to 55, wherein a yield of said second population of corn plants is equal to or more than a yield of said first population of corn plants.

Embodiment 57

A method of reducing a corn-on-corn yield penalty in a field grown in a corn-on-corn rotation for two or more consecutive growing seasons, comprising:
a. growing a first population of corn plants in said field during a first growing season; and
b. growing a second population of corn plants in said field during a second growing season; said second population of corn plants is treated with an inoculant comprising *Penicillium bilaii* prior to planting, at the time of planting and/or after planting, and wherein said first and second growing seasons are consecutive growing seasons.

Embodiment 58

The method of Embodiment 57, wherein said inoculant is applied to seeds of said second population of corn plants prior to planting.

Embodiment 59

The method of Embodiments 57 or 58, wherein said inoculant is applied to soil of said field prior to planting.

Embodiment 60

The method of any one of Embodiments 57 to 59, wherein said inoculant is applied to seeds of said second population of corn plants at planting.

Embodiment 61

The method of any one of Embodiments 57 to 60, wherein said inoculant is applied to soil of said field after planting.

Embodiment 62

The method of any one of Embodiments 57 to 61, wherein said inoculant is applied to foliage of said second population of corn plants.

Embodiment 63

The method of any one of Embodiments 57 to 62, wherein a yield of said second population of corn plants is equal to or more than a yield of said first population of corn plants.

Embodiment 64

The method of any one of Embodiments 50 to 56, wherein said field was not fallow in said two or more consecutive corn growing seasons.

Embodiment 65

The method of any one of Embodiments 57 to 63 wherein said field was not fallow in said two or more consecutive corn growing seasons.

Embodiment 66

The method of any one of Embodiments 50 to 56, and 64, further comprising growing a third population of corn plants in said field in a third subsequent growing season wherein a yield of said third population of corn plants is at least equal to said first or said second populations of corn plants.

Embodiment 67

The method of any one of Embodiments 57 to 63, and 65, further comprising growing a third population of corn plants in said field in a third subsequent growing season wherein a yield of said third population of corn plants is at least equal to said first or said second populations of corn plants.

Embodiment 68

A method of crop rotation management that provides for two consecutive corn plantings in a field where the later planting provides a yield that is at least 80%, 82%, 84%, 86%, 88%, 90%, 92%, 94%, 96%, 98%, 100%, 102%, 104%, 106%, 108%, 110%, 115%, 120%, or 125% of the yield of the earlier planting, said method comprising:
a. treating corn seeds with an inoculant comprising an effective amount of *Penicillium bilaii*; and b. providing said treated corn seeds to a farmer for growing in a field in which corn was planted in an immediately preceding growing season.

Embodiment 69

The method of Embodiment 68, wherein said field is not intercropped in any one of the previous two, three, four, or five consecutive growing seasons.

Embodiment 70

The method of Embodiments 68 or 69, wherein a population of nitrogen-fixing plants is not grown in any one of the previous two, three, four, or five consecutive growing seasons.

Embodiment 71

The method of any one of Embodiments 68 to 70, wherein a population of nitrogen-fixing plants is not grown in the previous two consecutive growing seasons.

Embodiment 72

The method of any one of Embodiments 68 to 71, wherein a population of nitrogen-fixing plants is not grown in the previous three consecutive growing seasons.

Embodiment 73

The method of any one of Embodiments 68 to 72, wherein a population of nitrogen-fixing plants is not grown in the previous four consecutive growing seasons.

Embodiment 74

The method of any one of Embodiments 68 to 73, wherein a population of nitrogen-fixing plants is not grown in the previous five consecutive growing seasons.

Embodiment 75

The method of any one of Embodiments 68 to 74, wherein said nitrogen-fixing plants are leguminous plants.

Embodiment 76

The method of Embodiment 75, wherein said leguminous plants are soybean plants.

Embodiment 77

A method of reducing a corn-on-corn yield penalty, said method comprising:
a. planting corn seeds in need thereof that have been treated with an inoculant comprising *Penicillium bilaii* in a field in which corn was grown during a growing season that immediately precedes planting of said corn seeds in need thereof;
b. growing corn from said corn seeds in need thereof; and
c. producing a yield of corn wherein said corn-on-corn yield penalty is reduced as a result of said inoculant comprising *Penicillium bilaii*.

Embodiment 78

The method of Embodiment 77, wherein said yield of corn from said corn seeds in need thereof is greater than a yield of corn obtained from said corn field in the prior growing season that immediately precedes planting of said corn seeds in need thereof.

Embodiment 79

A method of reducing the corn-on-corn yield penalty, said method comprising:
a. administering, to a population of corn plants, corn seeds, and/or soil containing a population of corn plants or corn seeds in need thereof, an inoculant comprising an effective amount of *Penicillium bilaii*; and
b. growing said population of corn plants or corn seeds in need thereof in said soil; wherein corn was grown in said soil during a growing season that immediately precedes growth of said population of corn plant or corn seeds.

Embodiment 80

A method comprising:
a. planting corn seeds in soil in which corn was grown during a growing season that immediately precedes planting of said corn seeds; and
b. applying an inoculant comprising *Penicillium bilaii* to said soil, to said corn seeds and/or to plants that germinate from said corn seeds, wherein said inoculant is capable of increasing yield of said plants.

Embodiment 81

The method of Embodiment 80, wherein said inoculant is applied to said corn seeds prior to planting.

Embodiment 82

The method of Embodiments 80 or 81, wherein said applying is at least 0.25, 0.5, 0.75, 1, 2, 3, 4, 5, 6, 7, 8, 9, 10, 11, 12, 15, 18, 21, 24, 27, 30, 33, 36 months or more prior to planting.

Embodiment 83

The method of any one of Embodiments 80 to 82, wherein said inoculant is applied to said soil prior to planting.

Embodiment 84

The method of any one of Embodiments 80 to 83, wherein said inoculant is applied to said soil at planting.

Embodiment 85

The method of any one of Embodiments 80 to 84, wherein said inoculant is applied to said soil after planting.

Embodiment 86

The method of any one of Embodiments 80 to 85, wherein said inoculant is applied to foliage of said plants that germinate from said corn seeds.

Embodiment 87

The method of any one of Embodiments 80 to 86, wherein corn was sown in said soil for at least the previous two or more consecutive growing seasons.

Embodiment 88

The method of Embodiment 87, wherein said at least the previous two or more growing seasons is the previous three, four, five, six, seven, eight, nine, ten, or more growing seasons.

Embodiment 89

The method of Embodiments 87 or 88, wherein said method is capable of reducing a corn-on-corn yield penalty from consecutive corn planting by at least about 1, 2, 3, 4, 5, 10, 15, 20, 25, 30, 35, 40, 45, 50, 55, 60, 65, 70, 75, 80, 85, 90, 95%, or more.

Embodiment 90

The method of any one of Embodiments 80 to 87, wherein said corn-on-corn yield penalty is less than 20, 21, 22, 23, 23, 24, 25, 26, 27, 28, 29, 30, 35, 40, 45, or 50 bushels/acre.

Embodiment 91

The method of any one of Embodiments 80 to 90, wherein one or more characteristics of plant growth such as plant height, plant weight, number of cobs, cob weight, kernel number, kernel weight, and date to maturity, are enhanced by at least 1, 2, 3, 4, 5, 10, 15, 20, 25, 30, 35, 40, 45, 50, 55, 60, 65, 70, 75, 80, 85, 90, 95, 100, 125, 150, 175, 200, 250, 300%, or more.

Embodiment 92

The method of Embodiment 80, wherein said yield from said corn seeds is enhanced by at least 5, 10, 15, 20, 25, 30, 35, 40, 45, 50, 55, 60, 65, 70, 75, 80, 85, 90, 95, 100, 125, 150, 175, 200, 250, 300%, or more in relative to a corn yield from said previous growing season.

Embodiment 93

The method of any one of Embodiments 80 to 87, wherein no seeds of a population of non-corn plants were sown in the soil during any one of the previous 1, 2, 3, 4, 5, 6, 7, 8, 9, 10, or more growing seasons.

Embodiment 94

A method of maximizing a field's farming revenue, said method comprising:
a. determining a first projected net revenue from consecutive plantings of corn for at least two growing seasons in said field;
b. determining a second projected net revenue from a corn on non-corn rotation in said field for the same number of growing seasons;
c. determining a third projected net revenue from consecutive plantings of corn for at least two growing seasons in said field, wherein said third projected net revenue assumes that said corn and/or said field will be treated with an inoculant capable of reducing a corn-on-corn yield penalty in said field;
d. comparing said first, second and third projected net revenues;
e. recommending consecutive corn plantings; and
f. providing corn seeds treated with an inoculant comprising an effective amount of *Penicillium bilaii*.

Embodiment 95

The method of Embodiments 1, 23, 31, 36, 37, 50, 57, 68, 77, 79, 80, and 94, further comprising applying one or more compositions selected from the group consisting of one or more agronomically beneficial elements to the soil, one or more agronomically beneficial elements to the seed, one or more agronomically beneficial elements to the plant that germinates from the seed, one or more lipo-chitooligosaccharides (LCO), one or more chitooligosaccharides, one or more chitinous compounds, one or more isoflavonoids, jasmonic acid or derivatives thereof, linolenic acid or derivatives thereof, linoleic acid or derivatives thereof, one or more Karrakins, one or more pesticides, one or more fertilizers, and any combination of the above compositions.

Embodiment 96

The method of Embodiment 95, further comprising a microbe selected from the group consisting of the genera *Rhizobium* spp., *Acinetobacter, Arthrobacter, Arthrobotrys, Aspergillus, Azospirillum, Bacillus, Burkholderia, chryseomonas, Enterobacter, Eupenicillium, Exiguobacterium, Klebsiella, Kluyvera, Microbacterium, Mucor, Paecilomyces, Paenibacillus, Pseudomonas, Serratia, Stenotrophomonas, Streptomyces, Streptosporangium, Swaminathania, Thiobacillus, Torulospora, Vibrio, Xanthobacter*, and *Xanthomonas*.

Embodiment 97

A method comprising:
a. providing a farmer in need thereof with instructions for reducing a corn-on-corn yield penalty by applying an effective amount of an inoculant comprising *Penicillium bilaii* to a corn seed or to plants growing from said corn seed; and
b. providing to said farmer said inoculant.

Embodiment 98

The method of Embodiments 95 or 96, further comprising an isoflavonoid or isoflavone.

Embodiment 99

The method of Embodiments 95, 96, or 98 further comprising a pesticide selected from the group consisting of a fungicide, insecticide, or nematicide.

Embodiment 100

The method of Embodiment 1, wherein said inoculant further comprises a second microorganism, a pesticide, or a combination thereof.

Embodiment 101

The method of Embodiment 100, wherein said microorganism is selected from the group consisting of bacteria from the genera *Rhizobium, Bradyrhizobium, Azorhizobium, Sinorhizobium, Mesorhizobium*, and combinations thereof.

Embodiment 102

The method of Embodiments 100 or 101, wherein said second microorganism is applied at a rate of about $1 \times 10^2$, $5\times10^2$, $1\times10^3$, $5\times10^3$, $1\times10^4$, $5\times10^4$, $1\times10^5$, $5\times10^5$, $1\times10^6$, $5\times10^6$, $1\times10^7$, $5\times10^7$, or $1\times10^8$ colony forming units per seed.

Embodiment 103

The method of Embodiment 101, wherein said *Rhizobium* is selected from the group consisting of *R. cellulosilyticum*, *R. daejeonense*, *R. etli*, *R. galegae*, *R. gallicum*, *R. giardinii*, *R. hainanense*, *R. huautlense*, *R. indigoferae*, *R. leguminosarum*, *R. loessense*, *R. lupini*, *R. lusitanum*, *R. meliloti*, *R. mongolense*, *R. miluonense*, *R. sullae*, *R. tropici*, *R. undicola*, and *R. yanglingense*.

Embodiment 104

The method of Embodiment 101, wherein said *Bradyrhizobium* is selected from the group consisting of *B. bete*, *B. canariense*, *B. elkanii*, *B. iriomotense*, *B. japonicum*, *B. jicamae*, *B. liaoningense*, *B. pachyrhizi*, and *B. yuanmingense*.

Embodiment 105

The method of Embodiment 101, wherein said *Azorhizobium* is selected from the group consisting of *A. caulinodans* and *A. doebereinerae*.

Embodiment 106

The method of Embodiment 101, wherein said *Sinorhizobium* is selected from the group consisting of *S. abri*, *S. adhaerens*, *S. americanum*, *S. aboris*, *S. fredii*, *S. indiaense*, *S. kostiense*, *S. kummerowiae*, *S. medicae*, *S. meliloti*, *S. mexicanus*, *S. morelense*, *S. saheli*, *S. terangae*, and *S. xinjiangense*.

Embodiment 107

The method of Embodiment 101, wherein said *Mesorhizobium* is selected from the group consisting of *M. albiziae*, *M. amorphae*, *M. chacoense*, *M. ciceri*. *M. huakuii*, *M. loti*, *M. mediterraneum*, *M. pluifarium*, *M. septentrionale*, *M. temperatum*, and *M. tianshanense*.

Embodiment 108

The method of any one of Embodiments 100 to 102, wherein said pesticide is selected from the group consisting of an insecticide, a fungicide, a nematicide, and combinations thereof.

Embodiment 109

The method of Embodiment 108, wherein said fungicide is selected from the group consisting of pyraclostrobin, propiconazole, trifloxystrobin, azoxystrobin, fluxapyroxad, and combinations thereof.

Embodiment 110

The method of Embodiment 1, wherein said corn seeds are treated with a composition selected from the group consisting of cyantraniliprole, thiamethoxam, clothianidin, imidacloprid, sedaxane, azoxystrobin, fludioxonil, metalaxyl, mefenoxam, thiabenzole, prothioconazole, fluoxastrobin, fluxapyroxad, fluopyram, pyraclostrobin, VOTiVO™, LCO, *Bradyrhizobium japonicum*, and combinations thereof.

Embodiment 111

The method of Embodiment 1, wherein said population of corn plants are further treated with a composition selected from the group consisting of a fungicide, herbicide, insecticide, acaricide, nematicide, and a combination thereof.

Embodiment 112

The method of Embodiment 111, wherein said fungicide is selected from the group consisting of pyraclostrobin, propiconazole, trifloxystrobin, azoxystrobin, fluxapyroxad, and combinations thereof.

EXAMPLES

Example 1

It is well documented that planting continuous corn (corn after corn in consecutive planting seasons (non-rotated crops)) demonstrates an increasing yield penalty from year to year. For example, the study reported in Gentry et al., Agron. J., 105(2): 295-303 (2013) as shown in FIG. 1, correlates corn-on-corn yield penalty with the number of years in continuous corn planting, and shows that corn-on-corn yield penalty continues to increase with each year of continuously planting of corn.

Example 2

Four fields are established (F1, F2, F3, and F4), with F1 for consecutive corn-on-corn planting (CC), F2 for CC provided with an effective amount of inoculant comprising *Penicillium bilaii*, F3 for corn-on-soybean planting (CS), and F4 for CS with an effective amount of inoculant comprising *Penicillium bilaii*. The crops are cultivated in two consecutive growing seasons (GS1 and GS2).

F1, F2, F3, and F4 are managed with standard agronomic practices.

For yield determination at physiological maturity, plots are harvested utilizing standard research equipment. The CC yield penalty (CCYP) in a given growing season is calculated by subtracting the yield for CC from that for CS:

$$CCYP = Y_{CS} - Y_{CC}$$

The following table summarizes the study:

| Field | Crop planting | GS1 | GS2 | *Penicillium bilaii* in GS2 | Yield at GS2 | CCYP |
|---|---|---|---|---|---|---|
| F1 | CC | Corn | Corn | − | $Y_{CC}$ | $Y_{CS} - Y_{CC}$ |
| F2 | CC (Pb) | Corn | Corn | + | $Y_{CC(Pb)}$ | $Y_{CS} - Y_{CC(Pb)}$ |
| F3 | CS | Soybean | Corn | − | $Y_{CS}$ | N/A |
| F4 | CS (Pb) | Soybean | Corn | + | $Y_{CS(Pb)}$ | N/A |

At GS2, the CC corn yield when provided with an effective amount of *Penicillium bilaii* is greater than the CC corn yield with no *Penicillium bilaii* provided (i.e., $Y_{CC(Pb)} > Y_{CC}$). As a result, the CCYP in a CC planting is reduced when an effective amount of *Penicillium bilaii* is provided relative to a CC planting with no *Penicillium bilaii* provided (i.e., $(Y_{CS} - Y_{CC(Pb)}) < (Y_{CS} - Y_{CC})$).

$Y_{CC(Pb)}$ is at least 100%, 102%, 104%, 106%, 108%, 110%, 115%, 120%, or 125% of $Y_{CC}$.

In addition, at GS2, the CS corn yield when provided with an effective amount of *Penicillium bilaii* is greater than the CS corn yield with no *Penicillium bilaii* provided (i.e., $Y_{CS(Pb)} > Y_{CS}$).

Further, at GS2, the CS corn yield when provided with an effective amount of *Penicillium bilaii* is greater than the CC corn yield when provided with an effective amount of *Penicillium bilaii* (i.e., $Y_{CS(Pb)} > Y_{CC(Pb)}$).

Example 3

A *Penicillium bilaii* containing product was applied to corn seeds with a commercial fungicide and insecticide base seed treatment ("F/I") at an application rate of 0.4 oz per 100 pounds of corn seed. The control treatment used for comparison in each trial was the base fungicide and insecticide treated corn seed of the same hybrid represented in the *Penicillium bilaii* treatment. Field trials with a plot size of 4 rows by 100 ft long were conducted during 2013 at each of the 71 locations utilizing standard research methods and equipment. Some of these locations were planted to corn the previous growing season and were considered corn-on-corn rotation sites while other locations were planted to soybean the previous growing season and were considered corn-on-soy rotation sites. The experimental design was a Randomized Complete Block Design (RCBD) with four replications at each site. Corn yield data was analyzed post-harvest utilizing best linear unbiased estimation (BLUE) linear mixed model and the average yield was calculated for F/I only and F/I plus *Penicillium bilaii* treated seeds. Significance was determined by calculating p-values for F/I and F/I plus *Penicillium bilaii* treated conditions.

When averaged across all 71 locations, the F/I plus *Penicillium bilaii* treatment resulted in a positive yield delta over the F/I only control of 2.22 bu/A (p value=0.18). When only the corn-on-corn rotations locations were considered, the F/I plus *Penicillium bilaii* treatment resulted in a positive yield delta over the F/I only control of 5.19 bu/A (p value=0.03), which was a surprising result of significantly reducing the expected corn-on-corn yield penalty in the non-rotated corn fields.

Therefore, the results showed that the corn yield when provided with a *Penicillium bilaii* containing product was greater than the corn yield with no *Penicillium bilaii* containing product. As a result, the corn-on-corn yield penalty in the corn-on-corn planting was reduced when *Penicillium bilaii* was provided relative to a corn-on-corn planting without adding *Penicillium bilaii*.

Deposit of Biological Material

Applicant has made a deposit of two *Penicillium bilaii* strains disclosed herein with the Agricultural Research Service Patent Culture Collection, Northern Regional Research Center (NRRL), 1815 N. University Street, Peoria, Ill., 61604, USA. The deposit accession numbers for the two *Penicillium bilaii* strains are NRRL 50169 and NRRL 50162, and the date of deposit was Aug. 28, 2008 and Aug. 11, 2008, respectively. Access to the deposits will be available during the pendency of the application to the Commissioner of Patents and Trademarks and persons determined by the Commissioner to be entitled thereto upon request. The deposits will be maintained for a period of 30 years, or 5 years after the most recent request, or for the enforceable life of the patent, whichever is longer, and will be replaced if they become nonviable during that period. Applicant does not waive any infringement of rights granted under this patent.

What is claimed is:

1. A method for reducing a corn-on-corn yield penalty comprising the steps of:
    a. identifying a field in need of a reduction of a corn-on-corn yield penalty, wherein said field was planted with corn in the previous growing season;
    b. applying an inoculant comprising one or more *Penicillium bilaii* strains to a population of corn seeds in an amount that is between 0.25 to 1 fluid ounces per hundred weight (cwt) seed; and
    c. planting and growing said population in said field, wherein a population of corn plants grown in said field exhibits a reduced corn-on-corn yield penalty,
    wherein representative samples of said strains having been deposited with the Northern Regional Research Laboratory (NRRL 50169, NRRL 50162, NRRL 50776, NRRL 50777, NRRL 50778, NRRL 50779, NRRL 50780, NRRL 50781, NRRL 50782, NRRL 50783, NRRL 50784, NRRL 50785, NRRL 50786, NRRL 50787, and NRRL 50788) and the American Type Culture Collection (ATCC 20851, ATCC 22348, and ATCC 18309), and wherein said applying is coating said corn seeds with said inoculant prior to said planting.

2. The method of claim 1, wherein said one or more *Penicillium bilaii* strains are NRRL 50169 and NRRL 50162.

3. The method of claim 1, wherein said inoculant further comprises a *Penicillium* fungus selected from the group consisting of *P. albidum, P. aurantiogriseum, P. chrysogenum, P. citreonigrum, P. citrinum, P. digitatum, P. frequentas, P. fuscum, P. gaestrivorus, P. glabrum, P. griseofulvum, P. implicatum, P. janthinellum, P. lilacinum, P. minioluteum, P. montanense, P. nigricans, P. oxalicum, P. pinetorum, P. pinophilum, P. purpurogenum, P. radicans, P. radicum, P. raistrickii, P. rugulosum, P. simplicissimum, P. solitum, P. variabile, P. velutinum, P. viridicatum, P. glaucum, P. fussiporus,* and *P. expansum*.

4. The method of claim 1, wherein said inoculant further comprises an agronomically acceptable carrier.

5. The method of claim 1, wherein said inoculant comprises an amount from $1.0 \times 10^6$ to $1.0 \times 10^8$ colony forming units (cfu) per hectare.

6. The method of claim 1, wherein said inoculant comprises an amount from $1.0 \times 10^6$ to $1.0 \times 10^8$ colony forming units (cfu) per pound of corn seeds.

7. The method of claim 1, wherein said inoculant further comprises at least 100 colony forming units (cfu) per seed of a second microorganism, a pesticide, or a combination thereof.

8. The method of claim 7, wherein said second microorganism is selected from the group consisting of:
    bacteria from the genera *Rhizobium*, selected from the group consisting of *R. cellulosilyticum, R. daejeonense, R. etli, R. galegae, R. gallicum, R. giardinii, R. hainanense, R. huautlense, R. indigoferae, R. leguminosarum, R. loessense, R. lupini, R. lusitanum, R. meliloti, R. mongolense, R. miluonense, R. sullae, R. tropici, R. undicola,* and *R. yanglingense;*
    bacteria from the genera *Bradyrhizobium*, selected from the group consisting of *B. betae, B. canariense, B. elkanii, B. iriomotense, B. japonicum, B. jicamae, B. liaoningense, B. pachyrhizi,* and *B. yuanmingense;* bacteria from the genera *Azorhizobium*, selected from the group consisting of *A. caulinodans* and *A. doebereinerae*;

bacteria from the genera *Sinorhizobium*, selected from the group consisting of *S. abri, S. adhaerens, S. americanum, S. aboris, S. fredii, S. indiaense, S. kostiense, S. kummerowiae, S. medicae, S. meliloti, S. mexicanus, S. morelense, S. saheli, S. terangae,* and *S. xinjiangense*; and bacteria from the genera *Mesorhizobium*, selected from the group consisting of *M. albiziae, M. amorphae, M. chacoense, M. ciceri, M. huakuii, M. lot, M. mediterraneum, M. pluifarium, M. septentrionale, M. temperatum,* and *M. tianshanense*; and combinations thereof.

9. The method of claim 1, wherein the method further comprises application of a source of phosphorus to said soil of said field.

10. The method of claim 1, wherein the yield of said corn grown in said field with said inoculant is at least 5% more than a yield of corn grown in a comparable field after one or more consecutive corn plantings without said inoculant.

11. The method of claim 1, wherein said field was not intercropped in any one of the previous two consecutive growing seasons.

12. The method of claim 1, wherein said population of corn plants or corn seeds are further treated with a fertilizer.

13. The method of claim 1, wherein said population of corn plants are further treated with a composition selected from the group consisting of a fungicide, herbicide, insecticide, acaricide, nematicide, and a combination thereof.

14. The method of claim 1, wherein said corn seeds are further treated with a composition comprising an insecticide selected from the group consisting of cyantraniliprole, thiamethoxam, clothianidin, imidacloprid, and any combination thereof.

15. The method of claim 1, further comprising applying one or more compositions selected from the group consisting of one or more agronomically beneficial elements to said soil, one or more agronomically beneficial elements to said seed, one or more agronomically beneficial elements to a plant that germinates from said seed, and any combination thereof.

16. The method of claim 1, wherein said inoculant further comprises a bacterium selected from the group consisting of the genera *Rhizobium, Acinetobacter, Arthrobacter, Azospirillum, Bacillus, Burkholderia, Chryseomonas, Enterobacter, Exiguobacterium, Klebsiella, Kluyvera, Microbacterium, Paenibacillus, Pseudomonas, Serratia, Stenotrophomonas, Streptomyces, Streptosporangium, Swaminathania, Thiobacillus, Vibrio, Xanthobacter,* and *Xanthomonas*.

17. The method of claim 1, wherein said inoculant is present in an amount from $10^{-15}$ grams (g)/seed to $10^{-6}$ g/seed.

18. The method of claim 1, wherein said field was previously planted to corn in the previous two consecutive growing seasons.

19. The method of claim 1, wherein said reduced corn-on-corn yield penalty is less than 20 bushels/acre.

20. The method of claim 1, wherein said reduced corn-on-corn yield penalty is less than 25 bushels/acre.

21. The method of claim 1, wherein said field is not intercropped in any one of the previous three growing seasons.

22. The method of claim 1, wherein said field is not intercropped in any one of the previous four growing seasons.

23. The method of claim 1, wherein said field is not intercropped in any one of the previous five growing seasons.

24. The method of claim 1, wherein said corn seeds are further treated with a composition comprising a fungicide selected from the group consisting of sedaxane, azoxystrobin, fludioxonil, metalaxyl, mefenoxam, thiabenzole, prothioconazole, fluoxastrobin, fluxapyroxad, fluopyram, pyraclostrobin, and any combination thereof.

25. The method of claim 1, wherein said corn seeds are further treated with a composition comprising a bacterium selected from the group consisting of *Bacillus firmus, Bradyrhizobium japonicum*, and a combination of *Bacillus firmus* and *Bradyrhizobium japonicum*.

26. The method of claim 1, further comprising applying one or more compositions selected from the group consisting of one or more lipo-chitooligosaccharides (LCO), one or more chitooligosaccharides, one or more chitinous compounds, jasmonic acid, a jasmonic acid derivative, linolenic acid, a linolenic acid derivative, linoleic acid, a linoleic acid derivative, one or more karrakins, and any combination thereof.

27. The method of claim 1, wherein said inoculant further comprises a fungus selected from the group consisting of the genera *Arthrobotrys, Aspergillus, Eupenicillium, Mucor, Paecilomyces,* and Torulospora.

28. A method for reducing a corn-on-corn yield penalty comprising the steps of:

a. identifying a field in need of a reduction of a corn-on-corn yield penalty, wherein said field was planted with corn in the previous growing season;

b. applying an inoculant comprising one or more *Penicillium bilaii* strains to a population of corn seeds in an amount that is between 0.25 to 1 fluid ounces per hundred weight (cwt) seed; and c. planting and growing said population in said field, wherein a population of corn plants grown in said field exhibits a reduced corn-on-corn yield penalty, wherein each of said one or more *Penicillium bilaii* strains has a 16S rDNA genomic sequence (16S sequence) that is at least 97% identical to a 16S sequence from a deposited *Penicillium bilaii* strain on the basis of 16S rDNA sequence identity, wherein said deposited strain is selected from the group consisting of ATCC 20851, NRRL 50169, ATCC 22348, ATCC 18309, NRRL 50162, NRRL 50776, NRRL 50777, NRRL 50778, NRRL 50779, NRRL 50780, NRRL 50781, NRRL 50782, NRRL 50783, NRRL 50784, NRRL 50785, NRRL 50786, NRRL 50787, NRRL 50788, and combinations thereof, and wherein said applying is coating said corn seeds with said inoculant prior to said planting.

29. The method of claim 28, wherein said one or more *Penicillium bilaii* strains are NRRL 50169 and NRRL 50162.

* * * * *